United States Patent
Bhalay et al.

(10) Patent No.: US 7,361,661 B2
(45) Date of Patent: *Apr. 22, 2008

(54) 8-QUINOLINXANTHINE AND 8-ISOQUINOLINXANTHINE DERIVATIVES AS PDE 5 INHIBITORS

(76) Inventors: Gurdip Bhalay, 61 Bamborough Close, Southwater, Horsham, West Sussex (GB) RH13 7XG; Stephen P Collingwood, 14 Fowler Close, Maidenbower, Crawley, West Sussex (GB) RH70 7UN; Robin A Fairhurst, 5 Greenacres, Ashington, West Sussex (GB) RH10 7UN; Sylvie F Gomez, 53 French Road, Redcliff, Surrey (GB) RH 1 2HR; Reto Naef, Juraweg 14, Rheinfelden, Switzerland (CH) 4310; David A Sandham, 121 Rusper Road, Horsham, West Sussex (GB) RH12 4BP ( * ) Notice: Subject to any disclaimer, the term of this patent is extended or adjusted under 35 U.S.C. 154(b) by 0 days.

This patent is subject to a terminal disclaimer.

(21) Appl. No.: 11/329,889

(22) Filed: Jan. 11, 2006

(65) Prior Publication Data

US 2006/0106214 A1 May 18, 2006

Related U.S. Application Data

(60) Continuation of application No. 10/937,639, filed on Sep. 9, 2004, now Pat. No. 7,019,136, which is a division of application No. 10/644,328, filed on Aug. 20, 2003, now Pat. No. 6,919,337, which is a continuation of application No. 10/240,481, filed as application No. PCT/EP01/03909 on Apr. 5, 2001, now abandoned.

(30) Foreign Application Priority Data

Apr. 7, 2000 (GB) ................. 0008694.2

(51) Int. Cl.
*A61K 31/522* (2006.01)
*C07D 473/04* (2006.01)
(52) U.S. Cl. .................. 514/263.1; 544/268
(58) Field of Classification Search .......... 514/263.1; 544/268
See application file for complete search history.

(56) References Cited

U.S. PATENT DOCUMENTS 2,879,271 A 3/1959 Kalischnigg 4,599,338 A 7/1986 Regnier et al. ............. 514/265

FOREIGN PATENT DOCUMENTS

| WO | WO 94/28902 | 12/1994 |
| WO | WO 99/62905 | 12/1999 |
| WO | WO 00/37061 | 6/2000 |

*Primary Examiner*—Kamal A. Saeed
(74) *Attorney, Agent, or Firm*—Novartis; John B. Alexander

(57) ABSTRACT

A compound of formula (I)

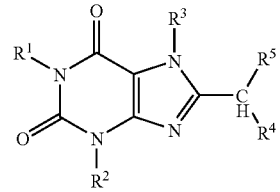

$R^1$ is hydrogen or alkyl optionally substituted by hydroxy, alkoxy, or alkylthio, $R^2$ is hydrogen, alkyl, hydroxyalkyl, alkylcarbonyloxyalkyl, alkoxyalkyl, alkylthioalkyl, alkenyl, cycloalkylalkyl, heterocyclylalkyl, aralkyl in which the aryl ring thereof is optionally fused to a 5-membered heterocyclic group or is optionally substituted by one or more substituents selected from alkoxy, amino, alkylamino, dialkylamino, acylamino, halogen, hydroxy, aminosulfonyl, alkylaminosulfonyl, dialkylaminosulfonyl, alkylsufonylamino or dialkylaminosulfonylamino, $R^3$ is hydrogen or alkyl optionally substituted by hydroxy, alkoxy, or alkylthio, $R^4$ is hydrogen or alkyl, $R^5$ is a quinolinyl, isoquinolinyl or oxodihydroisoquinolinyl group optionally fused to a 5-membered heterocyclic group and optionally substituted by one or more substituents selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —$N(R^6)R^7$, aryl optionally substituted by one or more substituents selected from halogen or alkoxy, or heteroaryl having 5 or 6 ring atoms attached through a ring carbon atom to the indicated carbon atom, and $R^6$ and $R^7$ are each independently hydrogen or alkyl optionally substituted by hydroxy or alkoxy or one of $R^6$ and $R^7$ is hydrogen and the other is acyl, or $R^6$ and $R^7$ together with the nitrogen atom to which they are attached denote a 5- or 66-mambered heterocyclyl group.

3 Claims, No Drawings

8-QUINOLINXANTHINE AND 8-ISOQUINOLINXANTHINE DERIVATIVES AS PDE 5 INHIBITORS

This Application is a continuation of U.S. patent application Ser. No. 10/937,639, filed Sep. 9, 2004, now issued as U.S. Pat. No. 7,019,136, which is a divisional of U.S. patent application Ser. No. 10/644,328, filed Aug. 20, 2003, now issued as U.S. Pat. No. 6,919,337, which is a continuation of U.S. patent application Ser. No. 10/240,481, filed Oct. 2, 2002, now abandoned, which is a 371 of PCT/EP01/03909, filed Apr. 5, 2001, which in their entirety are herein incorporated herein by reference.

This invention relates to organic compounds, their preparation and their use as pharmaceuticals.

In one aspect, the invention provides compounds of formula

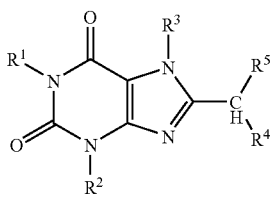

I in free or salt form, where
$R^1$ is hydrogen or alkyl optionally substituted by hydroxy, alkoxy, or alkylthio,
$R^2$ is hydrogen, alkyl, hydroxyalkyl, alkylcarbonyloxyalkyl, alkoxyalkyl, alkylthioalkyl, alkenyl, cycloalkylalkyl, heterocyclylalkyl, aralkyl in which the aryl ring thereof is optionally fused to a 5-membered heterocyclic group or is optionally substituted by one or more substituents selected from alkoxy, amino, alkylamino, dialkylamino, acylamino, halogen, hydroxy, aminosulfonyl, alkylaminosulfonyl, dialkylaminosulfonyl, alkylsufonylamino or dialkylaminosulfonylamino,
$R^3$ is hydrogen or alkyl optionally substituted by hydroxy, alkoxy, or alkylthio,
$R^4$ is hydrogen or alkyl,
$R^5$ is a quinolinyl, isoquinolinyl or oxodihydroisoquinolinyl group optionally fused to a 5-membered heterocyclic group and optionally substituted by one or more substituents selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —N($R^6$)$R^7$, aryl optionally substituted by one or more substituents selected from halogen or alkoxy, or heteroaryl having 5 or 6 ring atoms, attached through a ring carbon atom to the indicated carbon atom, and
$R^6$ and $R^7$ are each independently hydrogen or alkyl optionally substituted by hydroxy or alkoxy or one of $R^6$ and $R^7$ is hydrogen and the other is acyl, or $R^6$ and $R^7$ together with the nitrogen atom to which they are attached denote a 5- or 6-mambered heterocyclyl group.

"Alkyl" as used herein denotes straight chain or branched alkyl, which may be, for example, $C_1$-$C_{10}$-alkyl such as methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl or straight or branched decyl. Preferably alkyl is $C_1$-$C_8$-alkyl.

"Alkoxy" as used herein denotes straight chain or branched alkoxy which may be, for example, $C_1$-$C_{10}$-alkoxy such as methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, straight or branched octyloxy, straight or branched nonyloxy or straight or branched decyloxy. Preferably, alkoxy is $C_1$-$C_4$-alkoxy.

"Alkylthio" as used herein may be $C_1$ to $C_{10}$-alkylthio such as methylthio, ethylthio, n-propylthio, isopropylthio, n-butylthio, sec-butylthio, isobutylthio, tert-butylthio, pentylthio, hexylthio, heptylthio, octylthio, nonylthio or decylthio. Preferably alkylthio is $C_1$ to $C_4$-alkylthio.

"Alkenyl" as used herein means straight chain or branched alkenyl, which may be, for example, $C_2$ to $C_{10}$-alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$ to $C_4$-alkenyl.

"Cycloalkylalkyl" as used herein denotes alkyl, for example $C_1$ to $C_{10}$-alkyl such as one of the $C_1$ to $C_{10}$-alkyl groups hereinbefore mentioned, substituted by a $C_3$ to $C_8$ cycloalkyl group such as cyclopropyl, methylcyclopropyl, cyclobutyl, cyclopentyl, cyclohexyl, methylcyclohexyl, dimethylcyclohexyl, cycloheptyl or cyclooctyl. Preferably, cycloalkylalkyl is $C_3$-$C_6$-cycloalkyl-$C_1$-$C_4$-alkyl.

"Heterocyclylalkyl" as used herein denotes alkyl, for example $C_1$ to $C_{10}$-alkyl such as one of the $C_1$ to $C_{10}$-alkyl groups hereinbefore mentioned, substituted by a 5- or 6-membered heterocyclyl group having one or two hetero atoms selected from nitrogen, oxygen and sulfur in the ring, such as pyrrolyl, pyrrolidinyl, furyl, thienyl, pyridyl, piperidyl, imidazolyl, imidazolidinyl, pyrazolidinyl, piperazinyl, morpholinyl, oxazolyl, or furazanyl. Preferably, heterocyclylalkyl is $C_1$-$C_4$-alkyl substituted by a 5- or 6-membered heterocyclyl group having one or two nitrogen or oxygen atoms or one nitrogen atom and one oxygen atom in the ring.

"Aralkyl" as used herein means $C_6$-$C_{10}$-aryl-$C_1$-$C_{10}$ alkyl and may be, for example, one of the $C_1$-$C_{10}$-alkyl groups mentioned hereinbefore, particularly one of the $C_1$-$C_4$-alkyl groups, substituted by phenyl, tolyl, xylyl or naphthyl. Preferably, aralkyl is phenyl-$C_1$-$C_4$-alkyl, particularly benzyl or 2-phenylethyl.

"Acyl" as used herein denotes alkylcarbonyl, for example $C_1$-$C_{10}$-alkylcarbonyl where $C_1$-$C_{10}$-alkyl may be one of the $C_1$-$C_{10}$-alkyl groups hereinbefore mentioned, optionally substituted by one or more halogen atoms; cycloalkylcarbonyl, for example $C_3$-$C_8$-cycloalkylcarbonyl where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$-$C_{10}$-arylcarbonyl such as benzoyl; or aralkylcarbonyl, for example $C_6$ to $C_{10}$-aryl-$C_1$-$C_4$-alkylcarbonyl such as benzylcarbonyl or phenylethylcarbonyl. Preferably acyl is $C_1$-$C_4$-alkylcarbonyl.

"Alkynyl" as used herein denotes straight or branched alkynyl, for example $C_2$ to $C_6$-alkynyl such as ethynyl, propargyl, 2-butynyl, pentynyl or hexynyl. Preferably alkynyl is $C_2$-$C_4$-alkynyl.

"Aryl" as used herein denotes a monovalent carbocylic aromatic group, for example $C_6$-$C_{10}$-aryl such as phenyl, phenyl substituted by one or more, e.g. one, two or three, $C_1$-$C_4$-alkyl groups, or naphthyl. Preferably aryl is phenyl.

"Heteroaryl having 5 or 6 ring atoms" as used herein denotes a monovalent aromatic heterocyclic group having 5 or 6 ring atoms of which one, two or three are selected from nitrogen, oxygen and sulfur, such as pyrrolyl, furyl, thienyl, pyridyl, pyrazolyl, imidazolyl, triazolyl, oxazolyl, isoxazolyl, thiazolyl, isothiazolyl, dithiazolyl, tritbiazolyl, furazanyl, pyrazinyl, pyrimidinyl or triazinyl.

In alkylamino, dialkylamino, acylamino, dialkylaminosulfonylamino, alkylcarbonyl, alkylcarbonyloxy, alkoxycarbonyl, hydroxyalkyl, alkylthioalkyl and alkoxyalkyl, the alkyl, acyl or alkoxy groups as appropriate have the meanings hereinbefore described.

"Halogen" as used herein may be fluorine, chlorine, bromine or iodine; preferably it is fluorine, chlorine or bromine.

The 5-membered heterocyclic ring to which $R^5$ as a quinolinyl, isoquinolinyl or oxodihydroisoquinolinyl group is optionally fused may be, for example, a 5-membered heterocyclic ring having one or two hetero atoms in the ring, said hetero atoms being selected from oxygen, nitrogen and sulfur. Examples of such heterocyclic rings include pyrrole, pyrroline, pyrrolidine, furan, dihydrofuran, tetrahydrofuran, thiophene, dihydrothiophene, tetrahydrothiophene, imidazole, imidazoline, imidazolidine, pyrazole, pyrazoline, pyrazolidine, dioxolane, oxazole, isoxazole, thiazole and isothiazole rings. Preferably the 5-membered heterocyclic ring is a saturated ring having two hetero atoms, preferably two oxygen or two nitrogen atoms, especially two oxygen atoms.

$R^5$ as a quinolinyl group may be a 2-quinolinyl, 3-quinolinyl, 4-quinolinyl, 5-quinolinyl, 6-quinolinyl, 7-quinolinyl or 8-quinolinyl group, preferably a 4-quinolinyl, 5-quinolinyl or 8-quinolinyl group. $R^5$ as an isoquinolinyl group may be a 1-isoquinolinyl, 3-isoquinolinyl, 4-isoquinolinyl, 5-isoquinolinyl, 6-isoquinolinyl, 7-isoquinolinyl, or 8-isoquinolinyl group, preferably a 1-isoquinolinyl or 4-isoquinolinyl group. In most of the especially preferred embodiments of the invention, $R^5$ is a 4-isoquinolinyl group.

$R^5$ as a substituted quinolinyl or isoquinolinyl group is preferably substituted by one, two, three or four of the abovementioned substituents, especially one, two or three of those substituents. The preferred substituted 4-isoquinolinyl group is preferably substituted in the 1- and/or 6- and/or 7- and/or 8-position of the isoquinoline ring system.

In especially preferred embodiments of the invention, $R^5$ is a quinolinyl group of formula

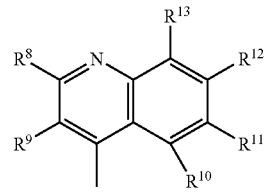

II or an isoquinolinyl group of formula

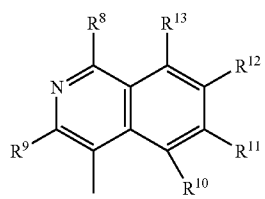

III where $R^8$, $R^9$, $R^{10}$, $R^{11}$, $R^{12}$ and $R^{13}$ are each independently hydrogen or a substituent selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —N($R^6$)$R^7$, aryl optionally substituted by one or more substituents selected from halogen or alkoxy, or heteroaryl having 5 or 6 ring atoms, or $R^{11}$ and $R^{12}$ together with the carbon atoms to which they are attached denote a 5-membered heterocyclic group having two oxygen or nitrogen atoms in the ring, and $R^6$ and $R^7$ are as hereinbefore defined.

$R^5$ as an oxodihydroisoquinolinyl group preferably has the oxo group ortho to the ring nitrogen atom, preferably in the 1-position in the isoquinoline ring system. It is preferably linked to the remainder of the molecule of formula I via the ring carbon atom meta to the ring nitrogen atom, i.e. the 4-position in the isoquinoline ring system. An especially preferred oxodihydroisoquinolinyl group is of formula

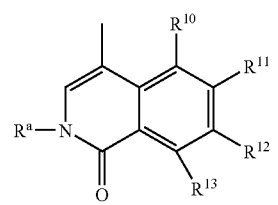

IIIA where $R^{10}$, $R^{11}$, $R^{12}$ and $R^{13}$ are as hereinbefore defined and $R^a$ is hydrogen or $C_1$-$C_4$-alkyl.

Preferred among the compounds of formula I in free or salt form are those where
$R^1$ is hydrogen or $C_1$-$C_4$-alkyl optionally substituted by hydroxy, $C_1$-$C_4$-alkoxy or $C_1$-$C_4$-alkylthio,
$R^2$ is hydrogen, $C_1$-$C_8$-alkyl, hydroxy-$C_1$-$C_8$-alkyl, $C_1$-$C_4$-alkylcarbonyloxy-$C_1$-$C_8$-alkyl, $C_1$-$C_4$-alkoxy-$C_1$-$C_8$-alkyl, $C_1$-$C_4$-alkylthio-$C_1$-$C_8$-alkyl, $C_2$-$C_4$-alkenyl, $C_3$-$C_8$-cycloalkyl-$C_1$-$C_4$-alkyl, heterocyclyl-$C_1$-$C_4$-alkyl where the heterocyclyl group is a 5- or 6-membered heterocyclyl group having one or two hetero atoms selected from nitrogen and oxygen atoms in the ring, phenyl-$C_1$-$C_4$-alkyl in which the phenyl ring is optionally substituted by one or more substituents selected from $C_1$-$C_4$-alkoxy, amino, $C_1$-$C_4$-alkylamino, di($C_1$-$C_4$-alkyl) amino, $C_1$-$C_4$-alkylcarbonylamino, halogen, $C_1$-$C_4$-alkylsulfonylamino, or di($C_1$-$C_4$-alkyl)aminosulfonylamino, and is optionally fused to a 5-membered heterocyclic ring having two oxygen or two nitrogen atoms in the ring, $R^3$ is hydrogen or $C_1$-$C_4$-alkyl optionally substituted by hydroxy, $C_1$-$C_4$-alkoxy or $C_1$-$C_4$-alkylthio, $R^4$ is hydrogen or $C_1$-$C_4$-alkyl, $R^5$ is a quinolinyl, isoquinolinyl or oxodihydroisoquinolinyl group optionally fused to a 5-membered heterocyclic group having two oxygen or two nitrogen atoms in the ring and optionally substituted by one or more substituents selected from halogen, cyano, carboxy hydroxy, $C_1$-$C_4$-alkyl, hydroxy-$C_1$-$C_4$-alkyl, $C_1$-$C_4$-alkoxy-$C_1$-$C_4$-alkyl, $C_1$-$C_4$-alkylthio-$C_1$-$C_4$-alkyl, $C_1$-$C_4$-alkoxy, $C_1$-$C_4$-alkylthio, $C_2$-$C_4$-alkenyl, $C_2$-$C_4$-alkynyl, $C_1$-$C_4$-alkylcarbonyl, a group —N($R^6$)$R^7$ or phenyl optionally substituted by one or more substituents selected from halogen or $C_1$-$C_4$-alkoxy and $R^6$ and $R^7$ are each independently hydrogen or $C_1$-$C_4$-alkyl optionally substituted by hydroxy or alkoxy, or one of $R^6$ and $R^7$ is hydrogen and the other is $C_1$-$C_4$-alkylcarbonyl, or $R^6$ and $R^7$ together with the nitrogen atom to which they are attached denote a 5- or 6-membered heterocyclyl group having one or two nitrogen atoms and, optionally, an oxygen atom in the ring.

Further preferred among the compounds of formula I are those where $R^1$ is hydrogen or $C_1$-$C_4$-alkyl, $R^2$ is hydrogen, $C_1$-$C_8$-alkyl, hydroxy -$C_1$-$C_8$-alkyl, or $C_1$-$C_4$-alkylcarbonyloxy-$C_1$-$C_8$-alkyl, $C_2$-$C_4$-alkenyl, $C_3$-$C_6$-cycloalkyl-$C_1$-$C_4$-alkyl, heterocyclyl-$C_1$-$C_4$-alkyl where the heterocyclyl group is a 5-membered heterocyclyl group having one nitrogen or oxygen atom in the ring, phenyl-$C_1$-$C_4$-alkyl in which the phenyl ring is optionally substituted by one or two substituents selected from $C_1$-$C_4$-alkoxy, amino, $C_1$-$C_4$-alkylcarbonylamino, chlorine, bromine, $C_1$-$C_4$-alkylsulfonylamino, or di($C_1$-$C_4$-alkyl)aminosulfonylamino and is optionally fused to a 5-membered heterocyclic ring having two oxygen atoms in the ring, $R^3$ is hydrogen or $C_1$-$C_4$-alkyl, $R^4$ is hydrogen or $C_1$-$C_4$-alkyl, $R^5$ is a quinolinyl group of formula II, an isoquinolinyl group of formula III or an oxodihydroisoquinolinyl group of formula IIIA, where $R^8$, $R^9$, $R^{10}$, $R^{11}$, $R^{12}$ and $R^{13}$ are each independently selected from hydrogen, halogen, cyano, carboxy, hydroxy, $C_1$-$C_4$-alkyl, hydroxy-$C_1$-$C_4$-alkyl, $C_1$-$C_4$-alkoxy-$C_1$-$C_4$-alkyl, $C_1$-$C_4$-alkylthio$C_1$-$C_4$-alkyoxy, $C_l$-$C_4$-alkylthio, $C_2$-$C_4$-alkenyl, $C_2$-$C_4$-alkynyl, $C_1$-$C_4$-alkylcarbonyl, a group —N($R^6$)$R^7$ or phenyl optionally substituted by one or two substituents selected from halogen or $C_1$-$C_4$-alkoxy, or $R^{11}$ and $R^{12}$ together with the carbon atoms to which they are attached denote a 5-membered heterocyclic group having two oxygen atoms in the ring, and $R^6$ and $R^7$ are each independently hydrogen or $C_1$-$C_4$-alkyl optionally substituted by hydroxy or alkoxy or one of $R^6$ and $R^7$ is hydrogen and the other is $C_1$-$C_4$-alkylcarbonyl, or $R^6$ and $R^7$ together with the nitrogen atom to which they are attached denote a 6-membered heterocyclyl group having one or two nitrogen atoms, or one nitrogen atom and one oxygen atom, in the ring.

Amongst the further preferred compounds hereinbefore described, especially preferred compounds are usually those in which $R^5$ is an isoquinolinyl group of formula III in which $R^8$ is hydrogen, $C_1$-$C_4$-alkyl, halogen, cyano, —N($R^6$)$R^7$ where $R^6$ and $R^7$ are independently $C_1$-$C_4$-alkyl or $R^6$ and $R^7$ together with the nitrogen atom to which they are attached denote a 6-membered heterocyclyl group having one or two nitrogen atoms, or one nitrogen atom and one oxygen atom, in the ring, or phenyl substituted by one or two $C_1$-$C_4$-alkoxy groups; $R^9$ and $R^{10}$ are each independently hydrogen, $C_1$-$C_4$-alkyl or halogen; $R^{11}$ and $R^{12}$ are each independently hydrogen, halogen, cyano, carboxy, hydroxy, $C_1$-$C_4$-alkyl, $C_1$-$C_4$-alkoxy or $C_2$-$C_4$-alkynyl, or $R^{11}$ and $R^{12}$ together with the carbon atoms to which they are attached denote a 5-membered heterocycle having two oxygen atoms in the ring; and $R^{13}$ is hydrogen or halogen.

Specific especially preferred compounds of formula I are those hereinafter described in the Examples. More preferred amongst these compounds are those of Examples 7, 10, 15, 35, 45, 49, 55, 60, 68 and 70.

Compounds of formula I may be in the form of salts, particularly pharmaceutically acceptable salts. Pharmaceutically acceptable acid addition salts of compounds of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for, example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. Pharmaceutically acceptable base salts of compounds of formula I where $R^3$ is hydrogen include metal salts, particularly alkali metal or alkaline earth metal salts such as sodium, potassium, magnesium or calcium salts, and salts with ammonia or pharmaceutically acceptable organic amines or heterocylic bases such as ethanolamines, benzylamines or pyridine. These salts may be prepared from free compounds of formula I or other salts of compounds of formula I by known salt-forming procedures.

The present invention also provides a process for the preparation of compounds of formula I in free or salt form which comprises 1) (a) dehydrating a compound of formula

IV

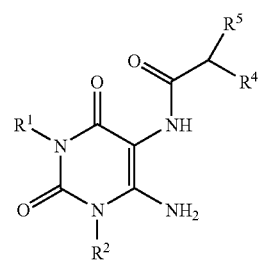

where $R^1$, $R^2$, $R^4$ and $R^5$ are as hereinbefore defined; or (b) for the preparation of a compound of formula I in free or salt form where $R^3$ is alkyl optionally substituted by hydroxy, alkoxy or alkylthio, reacting a compound of formula I in free or salt form with an appropriate alkylating agent, or (c) for the preparation of a compound of formula I in free or salt form where $R^2$ is aralkyl substituted in the aryl ring by alkylsulfonylamino or dialkylaminosulfonylamino, reacting a compound of formula I in salt form where $R^2$ is aralkyl substituted by amino with, respectively, an alkylsulfonyl halide or dialkylaminosulfonyl halide; or (d) for the preparation of a compound of formula I in free or salt form where $R^2$ is hydroxy-substituted alkyl, hydration of a compound of formula I where $R^2$ is alkenyl; or (e) for the preparation of a compound of formula I in free or salt form where $R^2$ is alkyl substituted by alkylcarbonyloxy, appropriate esterification of a compound of formula I where $R^2$ is hydroxy-substituted alkyl; or (f) for the preparation of a compound of formula I in free or salt form where $R^2$ is aralkyl substituted in the aryl ring by amino, hydrolysing a compound of formula I where $R^2$ is aralkyl substituted in the aryl ring by acylamino; or (g) for the preparation of a compound of formula I in free or salt form where $R^5$ is quinolinyl or isoquinolinyl substituted by hydroxy, dealkylation of a compound of formula I where $R^5$ is respectively quinolinyl or isoquinolinyl substituted by alkoxy, particularly methoxy; or (h) for the preparation of a compound of formula I in free or salt form where $R^5$ is quinolinyl or isoquinolinyl substituted by halogen, halogenation of a compound of formula I where $R^5$ is respectively quinolinyl or isoquinolinyl having an unsubstituted ring carbon atom available for halogenation; or (i) for the preparation of a compound of formula I in free or salt form where $R^2$ is a cyclopropyl group, optionally substituted by alkyl, subjecting a compound of formula I where $R^2$ is alkenyl to a Simmons Smith cyclopropanation reaction; and 2) recovering the resulting product of formula I in free or salt form.

Process (a) may be carried out by heating, or by reaction with an inorganic or organic base. It may be effected in an organic or aqueous solvent or mixed aqueous/organic solvent. The reaction with base may be carried out at ambient temperature or, more conveniently, at elevated temperature. The reaction is preferably carried out by treatment with aqueous alkali metal hydroxide in an alcoholic solvent at elevated temperature, for example as described hereinafter in the Examples. The compound of formula IV is preferably a compound where $R^5$ is a group of formula I or III. Compounds of formula IV may be prepared by reacting a compound of formula

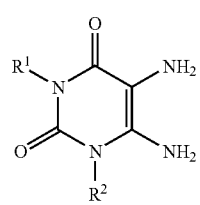

V where $R^1$ and $R^2$ are as hereinbefore defined, with a compound of formula

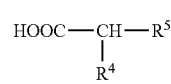

VI or an amide-forming derivative thereof, where $R^4$ and $R^5$ are as hereinbefore defined. The reaction may be effected by treating the carboxylic acid of formula VI with a peptide coupling agent to form in situ an activated ester or mixed anhydride, followed by treatment with the compound of formula V in an organic, e.g. dipolar aprotic, or mixed aqueous-organic (e.g. chlorohydrocarbon) solvent. The latter treatment may be carried out at sub-ambient, ambient or elevated temperature, conveniently at ambient temperature. Preferably, the acid of formula VI is treated with a carbodiimide derivative in the presence of hydroxybenzotriazole and, optionally, a base, or is treated with a benzotriazolyl-(trisdialkylamino)-oxyphosphonium salt. The resulting intermediate is preferably treated with the compound of formula V in a dipolar aprotic solvent or mixed chlorohydrocarbon-aqueous solvent at ambient temperature. Procedures may be as hereinafter described in the Examples.

Compounds of formula V may be prepared by reduction of a compound of formula

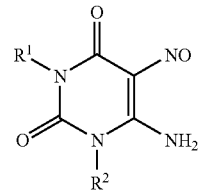

VII where $R^1$ and $R^2$ are as hereinbefore defined.

The reduction may be effected using known procedures, for example by treating the compound of formula VII with a reducing agent in an organic or aqueous solvent. The reaction may be carried out at ambient or, more conveniently, at elevated temperature. Preferred reducing agents are alkali metal dithionite salts in aqueous media or hydrogen in the presence of a noble metal catalyst. Treatment with sodium dithionite in aqueous solution at 80-90° C. is particularly preferred.

Compounds of formula VII may be prepared by nitrosation of a compound of formula

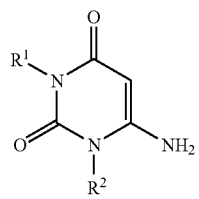

VIII where $R^1$ and $R^2$ are as hereinbefore defined, for example with an organic or inorganic nitrosating agent in an organic or aqueous or mixed organic-aqueous solvent. Nitrosation may be effected using known procedures at sub-ambient, ambient or elevated temperature, preferably with an alkali metal nitrite such as sodium nitrite in the presence of an acid such acetic acid at sub-ambient or ambient temperature, preferably in a mixed alcoholic-aqueous solvent such as aqueous ethanol.

Compounds of formula VIII may be prepared by reacting a compound of formula

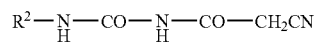
IX where $R^2$ is as hereinbefore defined with an inorganic or organic base to effect cyclisation, followed, where $R^1$ is an optionally substituted alkyl group, by reaction with an alkylating agent. The cyclisation reaction may be effected using conventional procedures. It is conveniently carried out in an aqueous, organic or mixed organic-aqueous solvent. Reaction may be effected at ambient or, more conveniently, elevated temperature. The base is preferably an alkali metal hydroxide, especially sodium hydroxide, which is preferably reacted in a mixed aqueous-alcoholic solvent, preferably at elevated temperature, e.g. 80-90° C. The optional alkylation step can be effected using known procedures, for example in the presence of an inorganic or organic base, for example in an aqueous, organic or mixed aqueous-organic solvent. Alkylation may be carried out at sub-ambient temperature or, more conveniently, at ambient or elevated temperature. Preferred alkylating agents are alkyl iodides or, especially, dialkyl sulfates. Preferred bases are alkali metal hydroxides in aqueous alcoholic solvents, especially aqueous ethanol.

Compounds of formula IX may be prepared by reacting a compound of formula

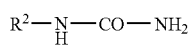
X with cyanoacetic acid or an amide-forming derivative thereof such as an ester or acid halide thereof, preferably the acid or its ethyl ester. The reaction may be effected using known procedures, for example in an organic solvent, preferably an anhydride such as acetic anhydride. The reaction temperature may be ambient or, more conveniently, elevated temperature, e.g. 65 to 70° C.

Compounds of formula X may be prepared using conventional procedures, for example from an isocyanate $R^2NCO$ by reaction with gaseous or aqueous ammonia or from an amine $R^2NH_2$ by reaction with a metal cyanate, for example as hereinafter described in the Examples.

Compounds of formula VIII where $R^1$ is alkyl optionally substituted by hydroxy, alkoxy or alkylthio and $R^2$ is as hereinbefore defined other than hydrogen, may be prepared by hydrogenolysis of a compound of formula

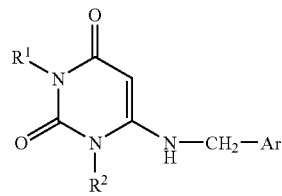
XI where $R^1$ is alkyl optionally substituted by hydroxy, alkoxy or alkylthio, $R^2$ is as hereinbefore defined other than hydrogen and Ar is phenyl optionally substituted by one or more $C_1$-$C_4$-alkoxy, preferably methoxy, groups. The hydrogenolysis may be carried out in a known manner, e.g. by treatment with hydrogen or a source of hydrogen and a metal catalyst such as a platinum or, preferably, palladium catalyst. The reaction may be carried out in an organic solvent. The reaction temperature may be ambient or elevated. Preferably hydrogenolysis is effected using palladium black in formic acid, e.g. as hereinafter described in the Examples.

Compounds of formula XI may be prepared by reacting a compound of formula

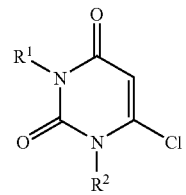
XII where $R^1$ and $R^2$ are as hereinbefore defined for formula XI, with a compound of formula $ArCH_2NH_2$ where Ar is as hereinbefore defined. The reaction may be carried out in a known manner, e.g. in an organic solvent, preferably an alcohol such as n-butanol, at ambient or elevated temperature, or analogously as hereinafter described in the Examples.

Compounds of formula XII may be prepared by reacting a compound of formula

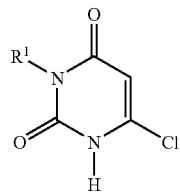
XIII where $R^1$ is as hereinbefore defined for formula XI, with a compound of formula $R^2X$ where $R^2$ is as hereinbefore defined for formula XI and X is halogen or hydroxy, where X is hydroxy, the reaction being carried out in the presence of activating reagents, preferably an azodicarboxylate such as di-t-butyl azodicarboxylate together with a triarylphosphine such as diphenylpyridylphosphine. The reaction may be carried out in an organic solvent, preferably an ether such as dioxan. The reaction temperature may be sub-ambient or, preferably, ambient or elevated temperature. The reaction may be carried out using the procedure of Mitsonobu, Synthesis 1981, 1, or analogously as hereinafter described in the Examples. Compounds of formula XIII are known or may be prepared by known procedures.

Compounds of formula VI may be prepared, for example, (i) from benzaldehyde or a substituted benzadehyde using the procedure of Dyke et al, Tetrahedron 1968, 24, 1467 or (ii) from an optionally substituted, N-protected 1,2-dihydroisoquinoline by reaction with a 2-oxo-carboxylic acid using the procedure of Dyke et al, Tetrahedron 1968, 24, 1467, optionally followed by conversion of the resulting carboxylic acid into a methyl ester and then an alkali metal salt using the procedure of J. March, Advanced Organic Chemistry, 4th Edition, Wiley, N.Y., 1992, pages 393 and 378 or (iii) from an optionally substituted quinoline or isoquinoline by reaction with a hydride reducing agent followed by a 2-oxo-carboxylic ester using the procedure of Minter et al, J. Org. Chem. 1988, 53, 2653 or (iv) by introducing substituents onto the N-containing ring of an acid of formula VI using the procedures of Janin and Biagani, Tetrahedron 1993, 39, 10305, or Ford et al, J. Med. Chem, 1985, 28, 164.

Certain preferred compounds of formula VI may be prepared by (i) the reaction sequence

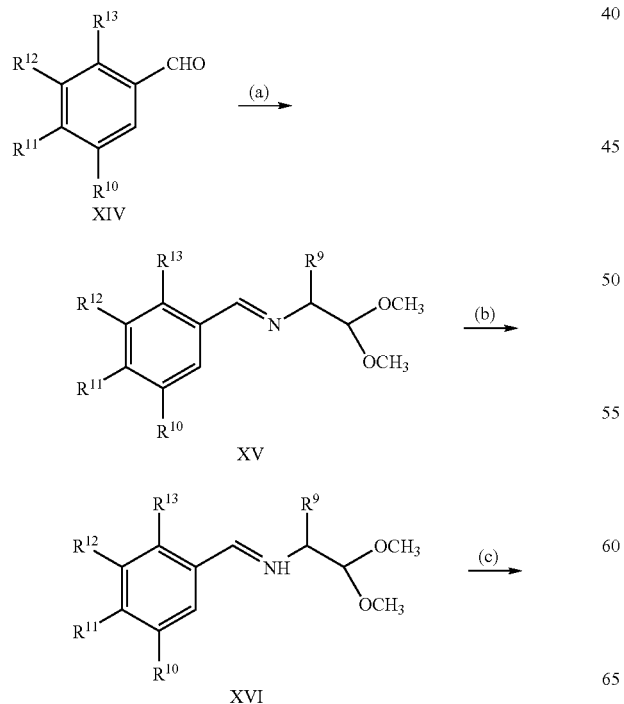

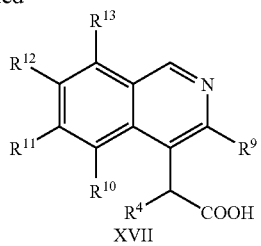

where $R^4$, $R^9$, $R^{10}$, $R^{11}$, $R^{12}$ and $R^{13}$ are as hereinbefore defined. Steps (a) to (c) may be carried out in a known manner, e.g. using the procedure of Dyke et al, Tetrahedron 1968, 24, 1467, or analogously as hereinafter described in the Examples;

(ii) the reaction sequence

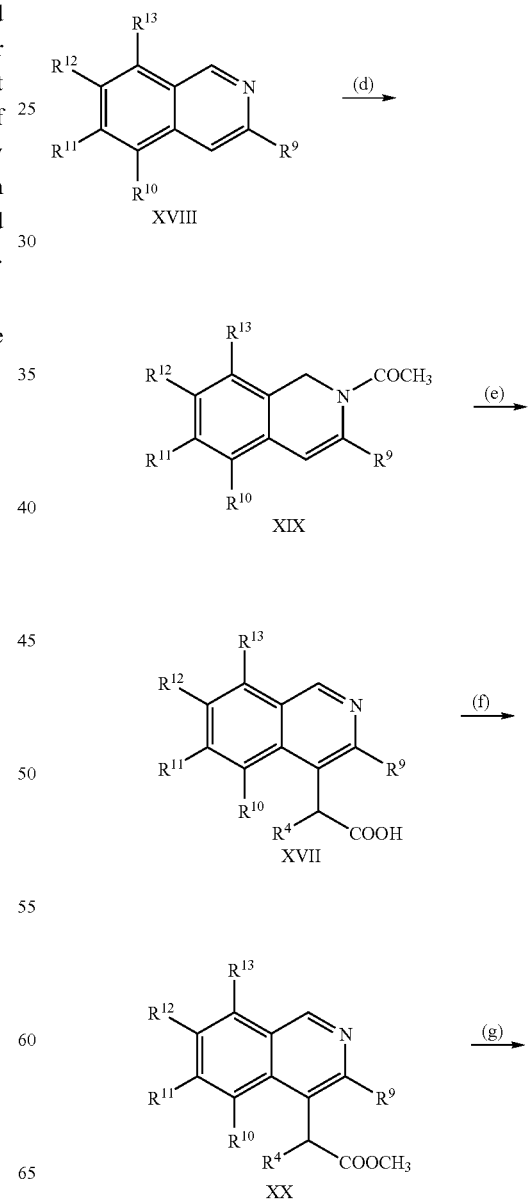

-continued

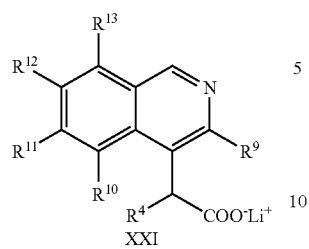
XXI where $R^1$, $R^9$, $R^{10}$, $R^{11}$, $R^{12}$ and $R^{13}$ are as hereinbefore defined. Steps (d) to (g) may be carried out in a known manner, e.g. step (d) using the procedure of Katayama et al, Chem. Pharm. Bull, 1980, 28, 2226, step (e) using the procedure of Dyke et al. Tetrahedron 1968, 24, 1467 and steps (f) and (g) using the procedure of J. March, Advanced Organic Chemistry, 4th Edition, Wiley, N.Y., 1992, pages 393 and 378, or analogously as hereinafter described in the Examples;

(iii) the reaction

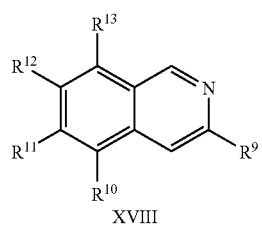
XVIII

→

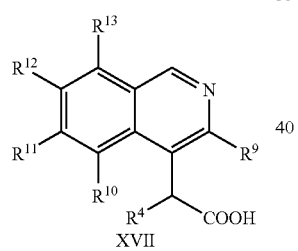
XVII e.g. by treatment of XVIII with a hydride reducing agent, followed by a 2oxo-carboxylic ester, using the procedure of Minter et al, J. Org. Chem. 1988, 53, 2653, or analogously as described hereinafter in the Examples;

(iv) for the preparation of compounds of formula VI in which $R^5$ is a 4-isoquinolinyl group substituted in the 1-position, the reaction sequence

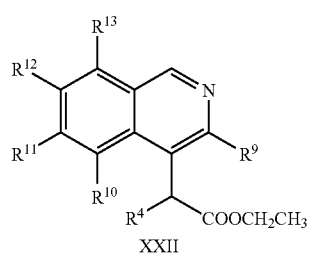
XXII (h) →

-continued

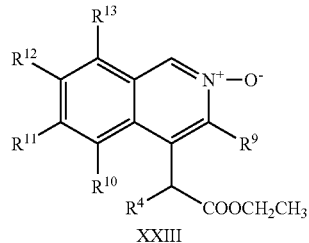
XXIII (i) →

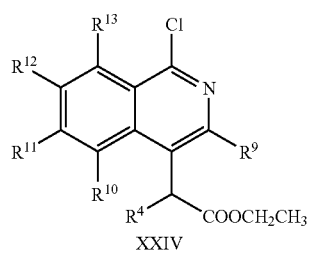
XXIV (j) →

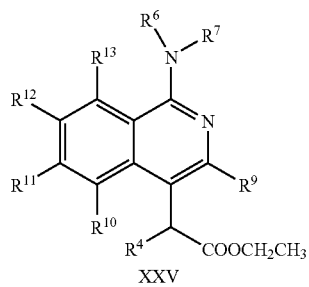
XXV (k) →

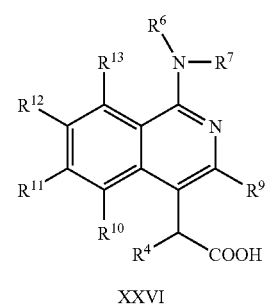
XXVI where $R^4$, $R^6$, $R^7$, $R^9$, $R^{10}$, $R^{11}$, $R^{12}$ and $R^{13}$ are as hereinbefore defined. Steps (h) to (k) may be carried out in a known manner, e.g. steps (h) to (j) using the procedure of Janin and Biagni, Tetrahedron, 1993, 39, 10305 and step (k) using the procedure of J. March, Advanced Organic Chemistry, 4th Edition, New York, 1992, page 378 or analogously as hereinafter described in the Examples;

(v) for the preparation of compounds of formula VI in which $R^5$ is an isoquinolinyl group of formula III in which $R^8$ is cyano, the reaction sequence

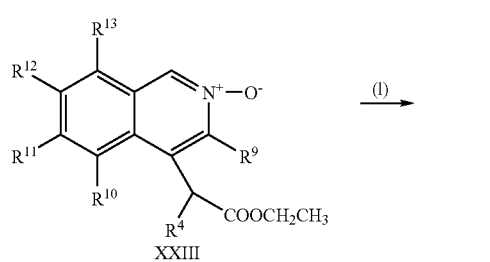
XXIII

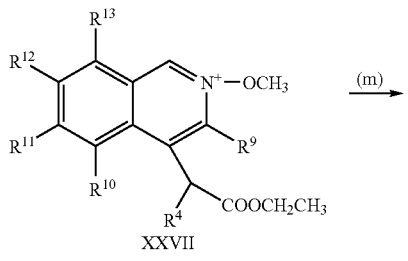
XXVII

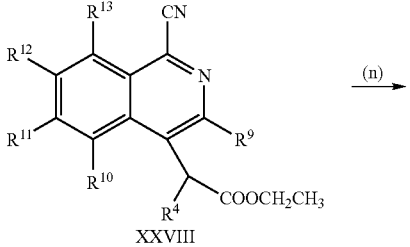
XXVIII

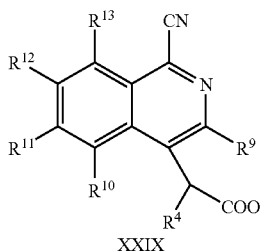
XXIX where $R^4$, $R^9$, $R^{10}$, $R^{11}$, $R^{12}$ and $R^{13}$ are as hereinbefore defined. Steps (l) to (n) may be carried out in a known manner, e.g. steps (l) and (m) using the procedure of Ford et al, J. Med. Chem., 1985, 28, 164 and step (n) using the procedure of J. March, op.cit., page 378;

(vi) for the preparation of compounds of formula VI in which $R^5$ is an oxodihydroisoquinolinyl group, the reaction sequence

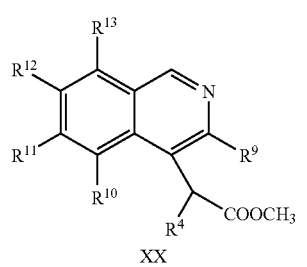
XX

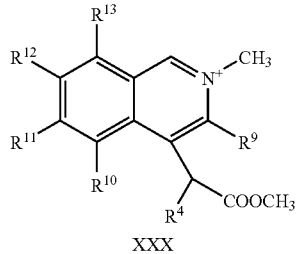
XXX

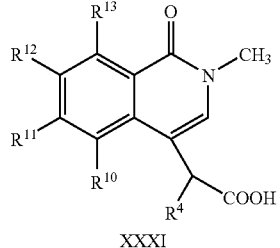
XXXI where $R^4$, $R^9$, $R^{10}$, $R^{11}$, $R^{12}$ and $R^{13}$ are as hereinbefore defined. Steps (o) and (p) may be carried out in a known manner, e.g. using the procedure of Holzgrabe, Arch. Pharm. (Weinheim, Ger.), 1988, 321, 767, or analogously as hereinafter described in the Examples;

(vii) for preparation of compounds of formula VI where $R^5$ is a quinolinyl group, the reaction

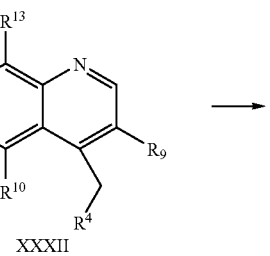
XXXII

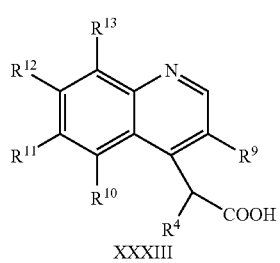
XXXIII where $R^4$, $R^9$, $R^{10}$, $R^{11}$, $R^{12}$ and $R^{13}$ are as hereinbefore defined, which may be carried out in a known manner, e.g. by treatment with a strong base, preferably an alkali metal dialkylamide such as lithium diisopropylamide, followed by treatment with carbon dioxide, e.g. using the procedure of using Brown and Curless, Tetrahedron Lett., 1986, 27, 6005, or analogously as hereinafter described in the Examples.

(viii) for the preparation of compounds of formula VI where R⁵ is a 4-isoquinolinyl group,

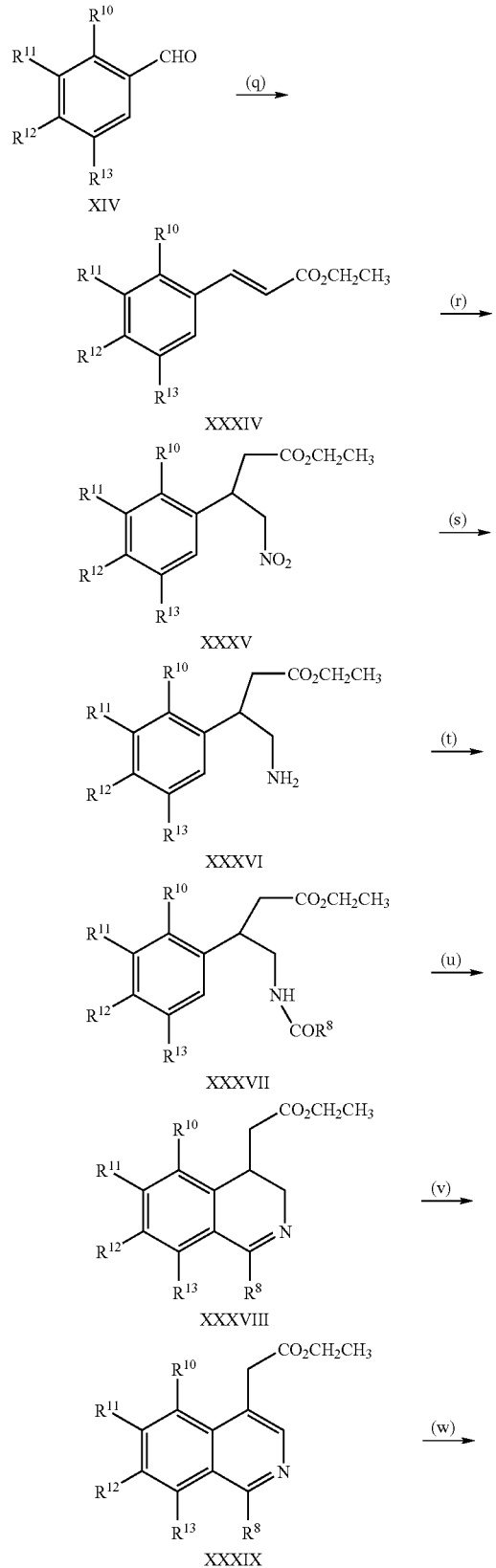

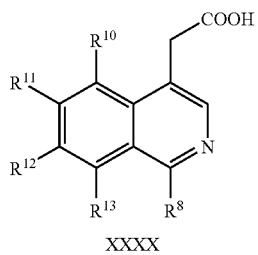

XXXX where $R^8$, $R^{10}$, $R^{11}$, $R^{12}$ and $R^{13}$ are as hereinbefore defined. Steps (q) to (w) may be carried out in a known manner; e.g. step (q) by treatment with a carboxyethyltriarylphosphonium ylid, preferably carboxyethyltriphenylphosphonium ylid in an organic solvent, preferably an ether or hydrocarbon, especially toluene, at sub-ambient, elevated or, preferably, ambient temperature; step (r) by treatment with nitromethane in the presence of an inorganic or, preferably, amine base, especially tetramethylguanidine, for example in the presence of a solvent or, preferably, in the absence of a solvent, at sub-ambient, ambient or, preferably, elevated temperature, e.g. 60-80° C.; step (s) by treatment with a reducing agent, preferably a tin (II) salt, especially tin (II) chloride hydrate, in an aqueous or, preferably, organic solvent, preferably an alcohol such as ethanol, at sub-ambient, ambient or, preferably, elevated temperature, e.g. wider reflux; step (t) by treatment with an acid halide or anhydride, preferably the acid chloride, of the acid $R^8COOH$, at elevated or, preferably, sub-ambient or ambient temperature, eg. 0° C. to ambient temperature, in an aqueous or, preferably, organic solvent, especially a chlorinated solvent such as dichloromethane, preferably in the presence of a base, especially an amine such as triethylamine; step (u) by treatment with a phosphorus (V) halide or oxyhalide, preferably phosphorous pentachloride or phosphorus oxychloride, preferably in an organic solvent such as a hydrocarbon or nitrile, especially acetonitrile, preferably at ambient or, especially, elevated temperature, e.g. under reflux; step (v) by treatment with a noble metal, preferably palladium, catalyst, preferably in an organic solvent, especially a hydrocarbon such as decalin, preferably at elevated temperature, e.g. under reflux; step (w) by treatment with an alkali metal hydroxide, preferably lithium or sodium hydroxide, in organic, aqueous or mixed organic-aqueous solvent, preferably THF-water, at sub-ambient, elevated or, preferably, ambient temperature; specific methods for steps (q) to (w) being as hereinafter described in the Examples.

(ix) the reaction sequence

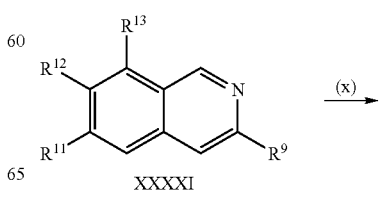

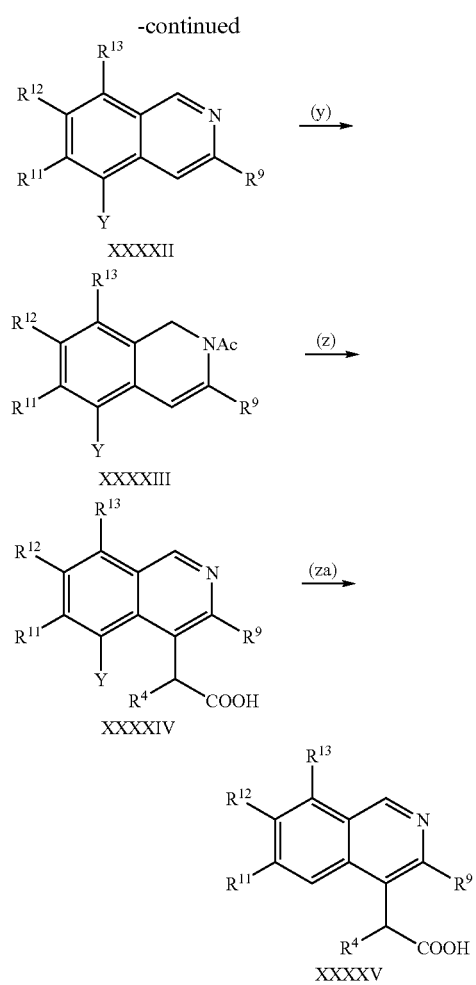

where $R^9$, $R^{11}$, $R^{12}$ and $R^{13}$ are as hereinbefore defined, Ac is an acyl group, and Y is halogen. Steps (x) to (za) may be effected in a known manner, e.g. step (x) by reaction with a halogenation agent, e.g. bromine or a N-halosuccinimide, preferably N-chlorosuccinimide, e.g. as described in J. March, op.cit., page 531; step (y) by reaction with a reducing agent, e.g. a metal hydride, in the presence of an acylating agent, e.g. acetic anhydride, e.g. as described in Katayama et al, op.cit; step (z) by reaction with a 2-oxocarboxylic acid, preferably glyoxylic acid, in the presence of a mineral acid, e.g. as described in Dyke et at, Tetrahedron 1968, 24, 1467; and step (za) by treatment with a reducing agent, e.g. as described in J. March et al, op.cit, page 566; or analogously as described hereinafter in the Examples.

Certain compounds of formula V are novel, including Intermediates 1 to 10 as described hereinafter. Certain compounds of formula VI are novel, including Intermediates 20 to 48 as described hereinafter.

Process variant (b) may be carried out in a known manner, for example by reacting a compound of formula I where $R^3$ is hydrogen with an appropriate alkylating agent, preferably an alkyl iodide or dialkyl sulfate, such as a compound of formula $R^3I$ or $(R^3)_2SO_4$ where $R^3$ is $C_1$-$C_4$-alkyl. The reaction may be conducted in the presence of an inorganic or organic base, for example in an aqueous, organic or mixed aqueous-organic solvent. Alkylation may be carried out at sub-ambient temperature or, more conveniently, at ambient or elevated temperature. Preferred bases are alkali metal carbonates. Preferred solvents are organic dipolar aprotic solvents, especially N,N-dimethylformamide.

Process variant (c) may be effected using known sulfonylation procedures, e.g. in the presence of an organic or inorganic base, preferably a tertiary organic base such as pyridine. The reaction temperature may be sub-ambient, ambient or, preferably, elevated. Preferred procedures are as hereinafter described in the Examples.

Process variant (d) may be effected using known procedures, e.g. by treating a compound of formula I wherein $R^2$ is alkenyl with a hydroborating agent, followed by oxidative basic work-up. Hydroboration may be carried out at sub-ambient or, more conveniently, at ambient or elevated, temperature. Preferred hydroborating agents are dialkylboranes such as 9-borabicyclo[2.2.0]nonane, which are preferably reacted under reflux. Oxidative work-up is preferably conducted with hydrogen peroxide and an alkali metal hydroxide, preferably sodium hydroxide. The work-up temperature is preferably 40-60° C.

Process variant (e) may be carried out using conventional esterification procedures, e.g. by reacting the compound of formula I wherein $R^2$ is hydroxy with a carboxylic acid or halide thereof, preferably an acid chloride, in the presence of an organic or inorganic base, at sub-ambient or, preferably, ambient or elevated (e.g. 40-60° C.) temperature. Preferred bases are organic tertiary bases such as pyridine.

Process variant (f) may be carried out using known procedures for conversion of acylamino into amino, e.g. by treatment with a mineral acid such as sulphuric or, preferably, hydrochloric acid. The reaction is preferably carried out in a mixed aqueous-organic solvent such as aqueous ethanol. The reaction temperature is conveniently ambient or, preferably, elevated temperature, especially reflux temperature.

Process variant (g) may be effected using known dealkylation methods, e.g. by reaction with HBr or HI, usually at elevated temperature, preferably by heating with concentrated hydrobromic acid, e.g. as hereinafter described in the Examples.

Process variant (h) may be effected using known halogenation procedures, e.g. by reaction with bromine or chlorine in a solvent such as acetic acid. The reaction is conveniently carried at ambient temperature, e.g. as hereinafter described in the Examples.

Process variant (i) may be effected using known procedures for the Simmons Smith reaction, e.g. by reaction with diethyl zinc and chloroiodomethane. The reaction is usually carried out in an organic solvent, preferably a halohydrocarbon. The reaction is suitably carried out at ambient temperature, e.g. as hereinafter described in the Examples.

Compounds of formula I in free form may be converted into salt form, and vice versa, in a conventional manner. The compounds in free or salt form can be obtained in the form of hydrates or solvates containing a solvent used for crystallization. The compounds of formula I in free or salt form can be recovered from reaction mixtures in a conventional manner. Isomer mixtures can be separated into individual isomers, e.g. enantiomers, in a conventional manner, e.g. by fractional crystallization.

Compounds of formula I in free or pharmaceutically acceptable salt form, hereinafter referred to alternatively as agents of the invention, are useful as pharmaceuticals. In particular, they are inhibitors of cyclic guanosine-3',5'-monophosphate phosphodiesterases (cGMP PDEs), especially PDE5. Agents of the invention are selective PDE5 inhibitors; in particular, they exhibit good selectivity for inhibition of PDE5 relative to inhibition of other phosphodiesterases, particularly PDE1 and PDE6, indicating a low side-effect profile.

Furthermore agents of the invention have an appropriate duration of action and many have a rapid onset of action. The inhibiting properties of agents of the invention may be demonstrated in the following test procedure:

PDE5 Assay: A 10 mM solution of a test compound in DMSO is diluted 100-fold with aqueous 20% v/v DMSO to give a 100 μM stock solution, which is further diluted with aqueous 20% v/v DMSO to give ten solutions having concentrations from 10 μM to 0.00051 μM. 10 μL of each of these solutions is transferred to a selected well of a 96-well Optiplate microtitre plate (ex Packard). To determine total binding, 10 μl of aqueous 20% v/v DMSO is added to other selected wells. To determine non-specific binding, a 10 mM solution of sildenafil in 100% DMSO is diluted 20-fold with aqueous 20% v/v DMSO and 10 μl of the resulting solution is added to further selected wells of the Optiplate plate. To all wells containing test compound solution, aqueous DMSO or sildenafil solution is added 80 μl of Assay Mix, prepared by mixing PDE Assay Buffer (2 ml), an aqueous solution of bovine serum albumin (BSA) containing 5 mg BSA/ml (2 ml), an aqueous 75 μM solution of cGMP sodium salt (0.2 ml), 3H-cGMP (ex Amersham, 10 μl) and distilled water (11.8 ml). (The PDE Assay Buffer is prepared by dissolving Tris-base (7.56 g) in water (800 ml), adding 1M aqueous $MgCl_2$ (10.325 ml) and 0.5 M EDTA (4.25 ml), adjusting the pH to 7.5 with 1N hydrochloric acid and making up to 1 litre with water). A solution of human PDE5, partially purified from human platelets (11 μl, containing 0.017 units of PDE5 per ml, where 1 unit hydrolyses 1.0 μmole of 3',5'-cyclic GMP to 5'-GMP per minute at pH 7.5 at 37° C.), in 20 mM Hepes, pH7.4, 100 mM sodium chloride, 10% v/v glycerol, 1 mM benzamidine and 2 mM dithiotherietol, is diluted 200-fold, with Enzyme Buffer prepared by adding 0.5M EDTA (2 ml) to a solution of Tris-Base (1.21 g) in water (800 ml), adjusting the pH to 7.5 with 1N HCl and making up to 1litre with water. The diluted PDE5 solution (10 μl) is added to all wells containing test compound, aqueous DMSO or sildenafil solution. The plate is incubated at room temperature for 1 hour. 50 μl of a suspension of 500 mg PDE Yttrium silicate SPA beads (ex Amersham) in 28 ml water is added to each of the wells and the plate is incubated for a further 20 minutes and then sealed using Top Seal-S (ex Packard) according to the manufacturer's instructions. The resulting scintillations are counted using a Canberra Packard Top Count (1 minute per well), as a measure of the extent to which binding of PDE5 to the beads is inhibited. The concentration of test compound at which 50% inhibition of PDE5 binding to the beads occurs ($IC_{50}$) is determined from concentration-inhibition curves in a conventional manner.

Compounds of the Examples hereinbelow have $IC_{50}$ values of the order of from 0.005 μM to 10 μM in the above assay. For example, the compounds of Examples 7, 10, 15, 35, 45, 49, 55, 60, 68 and 70 have $IC_{50}$ values of 0.007 μM, 0.01 μM, 0.006 μM, 0.010 μM, 0.002 μM, 0.0037 μM, 0.0055 μM, 0.0028 μM, 0.007 μM and 0.009 μM respectively in the above assay.

Having regard to their inhibition of PDE5, agents of the invention are useful in the treatment of conditions which are mediated by PDE5. Treatment in accordance with the invention may be symptomatic or prophylactic.

Accordingly, agents of the invention are useful in the treatment of sexual dysfunction, including male erectile dysfunction and female sexual dysfunction, premature labour, dysmenorrhoea, benign prostatic hyperplasia, bladder outlet obstruction, incontinence, stable, unstable and variant (Prinzmetal) angina, hypertension, pulmonary hypertension, congestive heart failure, atherosclerosis, conditions of reduced blood vessel patency, e.g. post-percutaneous transluminal coronary angioplasty, peripheral vascular disease, bronchitis, asthma, allergic rhinitis, glaucoma, tinnitus, diseases characterised by disorders of gut motility, e.g. irritable bowel syndrome, pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer, metastasis, baldness, nutcracker oesophagus, anal fissure and hypoxic vasoconstriction.

Agents of the invention are of particular interest for use in the treatment of sexual dysfunction, especially male erectile dysfunction.

In accordance with the foregoing, the invention also provides a method for the treatment of a condition mediated by PDE5, for example a condition mentioned hereinbefore, particularly sexual dysfunction, especially male erectile dysfunction, which comprises administering to a subject, particularly a human subject, in need thereof an effective amount of a compound of formula I in free form or in the form of a pharmaceutically acceptable salt. In another aspect, the invention provides a compound of formula I, in free form or in the form of a pharmaceutically acceptable salt, for use in the manufacture of, a medicament for the treatment of a condition mediated by PDE5, for example a condition as mentioned hereinbefore, particularly sexual dysfunction, especially male erectile dysfunction.

Agents of the invention may be administered by any appropriate route, e.g. orally, for example in the form of a tablet, a capsule, a solution or a suspension; parenterally, for example intravenously, intracavernosally, intramuscularly or subcutaneously; intranasally, for example in the form of an aerosol or aqueous dispersion; by inhalation, for example as an aerosol, a nebulized aqueous dispersion or a dry powder; buccally or sublingially, for example in the form of a tablet or lozenge; topically to the skin, for example in the form of a cream or ointment; or rectally, e.g. as a suppository.

In a further aspect the invention provides a pharmaceutical composition comprising as active ingredient a compound of formula I in free form or in the form of a pharmaceutically acceptable salt, optionally together with a pharmaceutically acceptable diluent or carrier therefor. Such compositions may be prepared using conventional excipients and techniques known in the galenic art. Thus oral dosage forms may include tablets and capsules. Compositions for inhalation may include aerosol or other atomizable formulations or dry powder formulations. Compositions for topical administration to the skin may include creams, ointments or gels.

The agents of the invention may also be used in combination with other PDE5 inhibitors or with other therapeutic agents suitable for the treatment of sexual dysfunction, particularly male erectile dysfunction, e.g. α adrenergic receptor antagonists such as phentolamine methanesulfonate, dopamine D2 agonists such as apomorphine or NO donors such as L-arginine. An agent of the invention may be mixed with the co-therapeutic agent in a pharmaceutical composition or it may be administered separately, before, simultaneously with or after the co-therapeutic agent.

This invention is illustrated by the following Examples. Intermediates of formula V are prepared as follows:

Intermediate 1

Methallylamine (211 g, 2.97 mol) is added to a solution of concentrated hydrochloric acid (250 ml) in water (1.9 l), followed by portionwise addition of potassium cyanate (240 g, 2.97 mol). The reaction is then heated for 2 hours at 80° C., prior to cooling and evaporation to afford (2-methyl-allyl)-urea (2445 g), mp 114-115° C. The urea (268 g, 2.35 mol) is added to a solution of cyanoacetic acid (220 g, 2.59 mol) in acetic anhydride, (536 ml) and the reaction is heated at 70° C. for 1 hour, cooled to 0° C. and diluted with ether. The resultant solid is collected by filtration, washed with ether, suspended in water (2.2 l) and heated to 75° C. 2M aqueous sodium hydroxide solution is then added portionwise over 30 min to maintain pH between 8 and 9.5. The reaction is cooled to room temperature, treated with acetic acid (12 ml), further cooled to 10° C. and the resultant solid is collected by filtration, washed with cold water and dried to afford 6-amino-1-(2-methyl-allyl)-1H-pyrimidine-2,4-dione, mp 267-269° C. The uracil (253 g, 1.40 mol) is added to a solution of sodium hydroxide (123 g, 3.07 mol) in water (2.5 l) and allowed to exotherm then cooled to 20° C. Dimethyl sulfate (196 ml, 2.06 mol) is added portionwise over 1 hour. After standing overnight, the reaction is cooled to 5° C. and the solid collected by filtration to give 6-amino-3-methyl-1-(2-methyl-allyl)-1H-pyrimidine-2,4dione, mp 162-163° C. The methyluracil (165 g, 0.85 mol) is suspended in water (1.55 l) and concentrated hydrochloric acid (72 ml). A solution of sodium nitrite (58.4 g, 0.85 mol) in water (117 ml) is then added dropwise over 30 minutes and the reaction is stirred at 20° C. for 3 hours. The solid is collected by filtration, washed successively with water, methanol and ether to afford 6-amino-3-methyl-1-(2-methyl-allyl)-5-nitroso-1H-pyrimidine-2,4dione, mp 213° C. (dec). The nitrosouracil (190 g, 0.85 mol) is suspended in water (950 ml), heated to 85° C. and sodium dithionite (85%, 347.2 g, 1.69 mol) is added portionwise. After cooling to room temperature, the solid is collected by filtration to afford 5,6-diamino-3-methyl-1-(2-methyl-allyl)-1H-pyrimidine2,4-dione, mp 152-153° C.

Intermediate 2

Using the general procedure for Intermediate 1, (3-nitrobenzyl)-urea [J. Med. Chem. 1996, 39, 1924] is converted into 6-amino-3-methyl-1-(3-nitro-benzyl)-1H-pyrimidine-2, 4-dione, [M-H]⁻ 275. A suspension of this compound (4.88 g, 17.7 mmol) and 10% Pd/C (0.484 g) in ethanol (200 ml) is hydrogenated at 1 atmosphere for 1.5 hours. The reaction mixture is filtered through a celite plug and evaporated to give 6-amino-1-(3-amino-benzyl)-3-methyl-1H-pyrimidine-2,4-dione acetic acid salt [M-H]⁻ 245. Acetic anhydride (1.85 ml, 19.57 mmol) is added to a cooled (0° C.) suspension of 6-amino-1-(3-amino-beryl)-3-methyl-1H-pyrimidine-2,4-dione acetic acid salt (5.01 g, 16.35 mmol) in pyridine (50 ml). The reaction mixture is warmed to room temperature, stirred for 6 hours and the solvent evaporated. The residue is triturated with water and the solid collected by filtration and dried to afford N-[3-(6-amino-3-methyl-2,4-dioxo-3,4-dihydro-2H-pyrimidin-1-ylmethyl)-phenyl]-acetamide, ¹H NMR (400 MHz, DMSO): δ: 2.00 (s 3H), 3.09 (s 3H), 4.72 (s 1H), 5.02 (s 2H), 6.75 (s 2H), 6.88 (d J 6 1H), 7.25 (t J 6 1H), 7.30 (s 1H), 7.55 (d J 6 1H). Using the general procedure for Intermediate 1, this compound is converted into N-[3-(5,6-diamino-3-methyl-2,4-dioxo-3,4-dihydro-2H-pyrimidin-1-ylmethyl)-phenyl]-acetamide [MH]⁺ 304.

Intermediate 3

Using the general procedure for Intermediate 1, (4-nitrobenzyl)-urea [J. Med. Chem. 1996, 39, 1924] is converted into 6-amino-3-methyl-1-(4-nitro-benzyl)-1H-pyrimidine-2, 4-dione, [MH]⁺ 277. A solution of calcium chloride (4.94 g, 45 mmol) in water (100 ml) is added to a solution of 6-amino-3-methyl-1-(4-nitro-benzyl)-1H-pyrimidine-2,4-dione (19.08 g, 69.0 mmol) in acetic acid (300 ml). Zinc dust (58.8 g, 900 mmol) is then added portionwise with external cooling. The reaction is stirred at room temperature for 1.5 hours, filtered through a celite plug and washed successively with ethanol and acetic acid. Evaporation of the combined filtrate and washings affords 6-amino-1-(4-amino-benzyl)-3-methyl-1H-pyrimidine-2,4-dione acetic acid salt, [M-3H]⁻ 243. Acetic anhydride (7.2 ml, 76.0 mmol) is added to a cooled (0° C.) suspension of 6-amino-1-(4-amino-benzyl)-3-methyl-1H-pyrimidine -2,4-dione acetic acid salt (17.0 g, 69.0 mmol) in pyridine (260 ml). The reaction mixture is warmed to room temperature, stirred for 6 hours and the solvent evaporated. The residue is triturated with water and the solid collected by filtration and dried to afford N-[4-(6-amino-3-methyl-2,4-dioxo-3,4-dihydro-2H-pyrimidin-1-ylmethyl)-phenyl]-acetamide, [MH]⁺ 289. Using the general procedure for Intermediate 1, this compound is converted into N-[4-(5,6-diamino-3-methyl-2,4-dioxo-3,4-dihydro-2H-pyrimidin-1-ylmethyl)-phenyl]-acetamide, [MH]⁺ 304.

Intermediate 4

To 2 cooled (0° C.) slurry of 6-chloromethyluracil (2.0 g, 12 mmol) in THF/dioxan (1:1, 16 ml) is added 2-pyridyldiphenylphosphine (3.60 g, 13.7 mmol) and cyclobutanemethanol (1.3 ml, 13.8 mmol), followed by di-t-butylazodicarboxylate (3.15 g, 13.7 mmol). The reaction is stirred overnight at ambient temperature, treated with 4M HCl in dioxan (15 ml) and evaporated. The residue is taken up in dichloromethane, washed with 3.5M HCl, dried over magnesium sulfate and evaporated. The crude product is purified by flash chromatography (100:1 dichloromethanemethanol elution) to afford 6-chloro-1-cyclobutylmethyl-3-methyl-1H-pyrimidine-2,4-dione, ¹H NMR (400 MHz, CDCl₃) δ

1.70-2.0 (m 6H), 2.60 (m 1H), 3.20 (s 3H), 4.00 (d J 7 2H), 5.78 (s 1H), which is dissolved in n-butanol (50 ml). Veratrylamine (4 ml, 26.5 mmol) is added and the reaction heated to reflux for 16 hours.

The solvent is evaporated and the residue taken into dichloromethane, washed with 1M aqueous HCl, dried over magnesium sulfate and evaporated. The crude product is purified by flash chromatography (50:1 dichloromethane-methanol elution) to afford 1-cyclobutylmethyl-6-(3,4dimethoxy-benzylamino)-3-methy-1H-pyrimidine-2,4-dione, $^1$H NMR (400 MHz, CDCl$_3$) d 1.60-1.80 (m 4H), 1.80-2.00 (m 2H), 2.50 (m 1H), 3.21, (s 3H), 3.80 (s 6H), 3.85 (d J 7 2H), 4.11 (d J 5 1H), 4.25 (m 1H), 4.84 (s 1H), 6.74 (s 1H), 6.80 (s 2H), which is dissolved in formic acid (50 ml) and Pd black (0.26 g) added. The reaction is heated at 40° C. for 21 hours, filtered through Celite, evaporated and purified by preparative HPLC to afford 6-amino-1-cyclobutylmethyl-3-methyl-1H-pyrimidine-2,4-dione, M$^+$ 209, which is converted using the general procedure for Intermediate 1 into 5,6-diamino-1-cyclobutylmethyl-3-methyl-1H-pyrimidine-2,4-dione, HPLC retention time 0.17 mins (30-95% acetonitrile water gradient in 4 minutes).

Intermediate 5

5,6-Diamino-3-methyl-1-(tetrahydro-furan-2-ylmethyl)-1H-pyrimidine-2,4-dione, mp 115-116° C., is prepared from (tetrahydro-furan-2-ylmethyl)-urea (Collect. Czech. Chem. Commun. 1972, 37, 2786) using the general procedure for Intermediate 1.

Intermediate 6

5,6-Diamino-3-methyl-1-(2-methyl-butyl)-1H-pyrimidine-2,4-dione, mp 163-165° C., is prepared using the general procedure for Intermediate 1.

Intermediate 7

5,6-Diamino-1-hexyl-3-methyl-1H-pyrimidine-2,4-dione, is prepared from 6-amino-1-hexyl-1H-pyrimidine-2,4-dione (J. Med. Chem. 1993, 36, 1465) using the general procedure for Intermediate 1, HPLC retention time (0-95% acetonitrile water gradient over 8 minutes) 6.01 min.

Intermediate 8

5,6Diamino-1-(3,4dimethoxy-benzyl)-3-methyl-1H-pyrimidine-2,4-dione, [M-H]$^-$ 305, is prepared from (3,4-dimethoxy-benzyl)-urea (Farmaco, Ed. Sci. 1977, 32, 813) using the general procedure for Intermediate 1.

Intermediate 9

5,6-Diamino-1-benzo[1,3]dioxol-5-ylmethyl-3-methyl-1H-pyrimidine-2,4dione, mp 183-186° C., is prepared using the general procedure for Intermediate 1.

Intermediate 10

5,6-Diamino-1-(2,4-dichloro-benzyl)-3-methyl-1H-pyrimidine-2,4 dione, is prepared using the general procedure for Intermediate 1, $^1$H NMR (400 MHz DMSO-d6) δ 3.16 (s 3H), 5.05 (s 2H), 6.18 (s 2H), 6.82 (d J 9 1H), 7.38 (d J 9 1H), 7.62 (s 1H).

Other Intermediates of formula V are prepared according to literature references as indicated below:

| No. | R$^1$ | R$^2$ | Reference |
|---|---|---|---|
| 11 | CH$_3$ | (CH$_3$)$_2$CHCH$_2$ | (1) |
| 12 | H | CH$_3$ | (2) |
| 13 | CH$_3$ | CH$_2$=CHCH$_2$ | (3) |
| 14 | CH$_3$ | cyclopropyl-CH$_2$ | (1) |
| 15 | CH$_3$ | (CH$_3$)$_3$CCH$_2$ | (1) |
| 16 | (CH$_3$)$_2$CHCH$_2$ | (CH$_3$)$_2$CHCH$_2$ | (1) |
| 17 | CH$_3$ | cyclohexyl-CH$_2$ | (1) |
| 18 | H | CH$_3$CH$_2$CH$_2$ | (2) |
| 19 | CH$_3$ | CH$_3$O-C$_6$H$_4$-CH$_2$ | (4) |

References:
(1) Eur. J. Med. Chem. 1990, 25, 653
(2) J. Med. Chem. 1996, 39, 2
(3) FR 2 531 085
(4) Eur. J. Med. Chem.-Chim. Ther. 1974, 9, 313

Intermediates of formula VI are prepared as follows:

Intermediate 20

A mixture of 3-(3,4-dimethoxy-phenyl)-5-nitro-pentanoic acid ethyl ester [J. Med. Chem, 1989, 32, 1450] (0.50 g, 1.68 mmol) and tin(II)chloride dihydrate (1.90 g, 8.4 mmol) in ethanol (10 ml) is heated to reflux for 2 hours, cooled to ambient temperature and evaporated. The crude product is taken into dichloromethane (15 ml), cooled to 0° C. and triethylamine (5 ml) added, followed by 3,5-methoxybenzoyl chloride (0.404 g, 2.02 mmol). The reaction is stirred at ambient temperature overnight and then evaporated, taken into ethyl acetate, washed with water and dried over sodium sulfate. Evaporation and purification by flash column chromatography (1:1 hexamethyl acetate elution) affords 4-(3,5-dimethoxy-benzoylamino)-3-(3,4-dimethoxy-phenyl)-butyric acid ethyl ester, [MH]$^-$ 432. This intermediate (0.200 g, 0.46 mmol) is taken into acetonitrile (8 ml) and phosphorus oxychloride (0.211 g, 1.38 mmol) added, prior to heating at reflux for 3 hours. After evaporation of the solvent, the residue is taken into ethyl acetate, washed with saturated aqueous sodium carbonate, dried over sodium sulfate and evaporated to afford [1-(3,5-dimethoxy-phenyl)-6,7-dimethoxy-3,4-dihydro-isoquinolin-4-yl]-acetic acid ethyl ester, [MH]$^+$ 414. This intermediate (0.5 g, 1.21 mmol) is dissolved in decalin (10 ml) and 10% Pd/C (50 mg) added. The reaction is heated at 190° C. for 2.5 hours, then cooled to ambient temperature and diluted with dichloromethane. After filtration through Celite, the combined filtrate and washings are evaporated to afford [1-(3,5-dimethoxy-phenyl)-6,7-dimethoxy-isoquinolin-4-yl]-acetic acid ethyl ester, $^1$H NMR (400 MHz, CDCl$_3$) δ 1.18 (t J 7 3H), 3.78 (s 6H), 3.80 (s 3H), 3.90 (s 2H), 3.99 (s 3H), 4.10 (q J 7 2H), 6.50 (d J 0.5 1H), 6.75, (d J 0.5 2H), 7.20 (s 1H), 7.36 (s 1H), 8.40 (s 1H). This intermediate (0.30 g, 0.73 mmol) is dissolved in methanol (10 ml), 1M aqueous lithium hydroxide (0.80 ml, 0.80 mmol) is added and the reaction stirred overnight at ambient temperature. After evaporation of the methanol, pH of the residual solution is adjusted to 7 with 1M aqueous HCl and the resultant solid collected by filtration and dried to afford [1-(3,5-dimethoxy-phenyl)-6,7-dimethoxy-isoquinolin-4-yl]-acetic acid.

Intermediate 21

A mixture of 3-isopropoxy4-methoxy-benzaldehyde (3.9 g, 20 mmol) and (ethoxycarbonylmethylene)triphenylphosphorane (6.96 g. 20 mmol) in toluene (100 ml) is heated at reflux for 2 hours, cooled to ambient temperature and evaporated. The crude product is taken in to dichloromethane and eluted through a pad of silica to afford (E)-3-(3-isopropoxy-4-methoxy-phenyl)-acrylic acid ethyl ester, TLC $R_f$ 0.70 (1:1 hexane-ethyl acetate). This intermediate is dissolved in nitromethane (10 ml), 1,1,3,3-tetramethylguanidine (0.5 ml) is added and the reaction heated at 70° C. for 36 hours. The solvent is evaporated, the residue is taken into ethyl acetate and washed with 2N aqueous HCl, water and brine. After drying over sodium sulfate and evaporation, the crude product is purified by flash column chromatography (4:1 hexane-ethyl acetate elution) to afford 3-(3-isopropoxy-4-methoxy-phenyl)-4-nitro-butyric acid ethyl ester, $^1$H NMR (400 MHz, CDCl$_3$) δ 1.20 (t J 7 3H), 1.38 (d J 7 6H), 2.75 (d J 6 2H), 3.90 (m 1H), 4.10 (m 2H), 4.48-4.78 (m 3H), 6.75-6.86 (m 3H). This intermediate is converted into [1-(3,5-diisopropoxy-phenyl)-6-isopropoxy-7-methoxy-isoquinolin4-yl]-acetic acid using the general procedure for Intermediate 20. Characterised as the ethyl ester, [MH]$^+$ 496.

Intermediate 22

A solution of 3-ethoxy-4-methoxybenzaldehyde (3.6 g, 20 mmol) in ethanol (15 ml) is added to 2,2-dimethoxyethylamine (21 mmol) and the mixture heated at reflux for 2 hours. After cooling to room temperature, sodium borohydride (0.794 g, 21 mmol) is added and the mixture stirred at room temperature overnight. Ethanol is removed by evaporation and water added, followed by extraction with ethyl acetate. The organic extracts are combined, washed with water, brine, dried over magnesium sulfate and evaporated to give (2,2-dimethoxy-ethyl)-(3-ethoxy-4-methoxy-benzyl)-amine, [MH]$^+$ 270. The intermediate (2.70 g, 10 mmol) is suspended in 6N HCl (50 ml), glyoxylic acid (0.88 g, 12 mmol) is added and the mixture heated for 1 hour at 100° C. After cooling to room temperature, methanol (30 ml) is added and the mixture filtered and characterised as the methyl ester M$^+$ 276. The filtrate is treated with lithium hydroxide (10 mmol) in THF-methanol-water overnight. After evaporation of the solvents, the crude product is partitioned between water and dichloromethane. The aqueous phase is washed with dichloromethane and evaporated to dryness to afford (7-ethoxy-6-methoxy-isoquinolin-4-yl)-acetic acid lithium salt which is used for xanthine formation without further characterisation.

Intermediate 23

A solution of (6,7-dimethoxy-isoquinolin-4-yl)-acetic acid ethyl ester (Tetrahedron 1973, 29, 3881) (1.668 g, 6.07 mmol) in chloroform (20 ml) is treated portionwise with m-chloroperoxybenzoic acid (1.153 g, 6.67 mmol) for 5 hours. The reaction mixture is washed with saturated sodium bicarbonate and brine, dried over MgSO$_4$ and evaporated to afford (6,7dimethoxy-2-oxy-isoquinolin-4-yl)-acetic acid ethyl ester 1.71 g, 96%). The entire product is dissolved in chloroform (30 ml), added to POCl$_3$ (3 ml, 32.3 mmol) and heated at reflux for 2 hours. After evaporation, dichloromethane and ice water are added and the mixture is basified with aqueous ammonia. The aqueous phase is further extracted with dichloromethane, the combined organic phases are washed with brine, dried over magnesium sulfate and evaporated to afford (1-chloro-6,7-dimethoxy-isoquinolin-4-yl)-acetic acid ethyl ester. The chloro ester derivative (0.50 g, 1.6 mmol) is suspended in 2M sodium hydroxide (15 ml). Ethanol (5 ml) is added and the solution stirred at room temperature for 2 hours and the solvent evaporated. Adjustment to pH 2 with concentrated hydrochloric acid affords a solid which is collected by filtration and dried to afford (1-chloro-6,7-dimethoxy-isoquinolin-4-yl)-acetic acid. $^1$H NMR (400 MHz, DMSO-d6) δ: 3.92 (s 3H), 3.96 (s 3H), 4.02 (s 2H), 7.31 (s 1H), 7.44 (s 1H), 8.04 (s 1H).

Intermediate 24

(2,2-Dimethoxy-ethyl)-(3-methoxy-benzyl)-amine (Tetrahedron, 1973, 29, 3881) is treated with pyruvic acid according to the general procedure for Intermediate 22 to afford 2-(7-methoxy-isoquinolin-4-yl)-propionic acid hydrochloride salt, mp 174-176° C. Treatment with HCl gas in ethanol affords the corresponding ethyl ester hydrochloride, mp 190-192° C., which is then reacted sequentially with m-chloroperoxybenzoic acid and phosphorus oxychloride as described for Intermediate 23 to provide 2-(1-chloro-7-methoxy-isoquinolin-4-yl)-propionic acid ethyl ester, mp 126-128° C. This intermediate (47 g, 0.16 mol): is dissolved in ethanol (400 ml) and 2N sodium hydroxide (150 ml) added and the mixture heated at 60° C. for one hour, prior to evaporation of the solvent. Crystallisation from acetone affords 2-(1-chloro-7-methoxy-isoquinolin-4-yl)-propionic acid, mp 167-168° C.

Intermediate 25

Dimethyl sulfate (12.7 ml, 0.10 mol) is added portionwise to 2-(7-methoxy-2-oxy-isoquinolin-4-yl)-propionic acid ethyl ester (28 g, 0.10 mol) with an exotherm to 100° C. The reaction is maintained at this temperature for 2 hours, cooled to room temperature and dissolved in water (50 ml). A solution of sodium cyanide (15 g, 0.31 mol) in water (90 ml) is added over 30 minutes with external cooling and the reaction is then stirred at room temperature for 3 hours. The crude product is extracted with chloroform, the chloroform extracts are washed with saturated sodium bicarbonate, brine, dried over sodium sulfate and evaporated. Crystallisation from 3N ethanolic HCl-ether affords 2-(1-cyano-7-methoxy-isoquinolin-4-yl)-propionic acid ethyl ester hydrochloride, mp 89-98° C. This compound is hydrolysed converted to the acid as described for Intermediate 22 and used directly crude for xanthine formation.

Intermediate 26

A solution of sodium triethylborohydride (1M THF, 12.7 ml, 12.7 mmol) is added dropwise to a solution of isoquinoline (1.64 g, 12.7 mmol) in THF (25 ml). The reaction is stirred at room temperature for 1 hour, prior to dropwise addition of a solution of ethyl glyoxalate (1.43 g, 13.9 mmol) in toluene (previously heated at 110° C. for 1.5 hours). After a further 4 hours at room temperature, the reaction is cooled to 0° C. and sodium hydroxide (0.5 M aqueous solution, 25.4 ml) followed by hydrogen peroxide (30% aqueous solution, 12.7 ml) is added, followed by stirring for 2 hours. The reaction is acidified with 1N HCl, washed with ethyl acetate three times, the aqueous phase is reduced in volume by evaporation and refrigerated overnight. The resultant precipitate is collected by filtration and dried to afford isoquinolin-4-yl-acetic acid hydrochloride salt, $MH^+$ 188.

Intermediate 27

Excess morpholine is added to a suspension of (1-chloro-6,7-dimethoxy-isoquinolin-4-yl)-acetic acid ethyl ester (0.200 g, 0.65 mmol) in toluene (1 ml) and the mixture heated to reflux until the starting material is consumed. After evaporation, the residue is partitioned between water and dichloromethane, the organic phase is dried over magnesium sulfate and evaporated to afford (6,7-dimethoxy-1-morpholin-4-yl-isoquinolin-4-yl)-acetic acid ethyl ester $[MH]^+$ 361. The crude ester (0.240 g, 0.66 mmol) is dissolved in ethanol (20 ml), treated with 2M sodium hydroxide (3 ml) and stirred at room temperature overnight. After adjustment to pH 1 with concentrated hydrochloric acid, the solvent is evaporated and the crude acid used directly for formation of the xanthine derivative.

Intermediate 28

The procedure for Intermediate 27 is repeated, using excess N-methylpiperazine in place of morpholine to afford [6,7-dimethoxy-1-(4-methyl-piperazin-1-yl)-isoquinolin-4-yl]acetic acid ethyl ester (0.186 g, 38%) $^1$H NMR (DMSO-6) δ 1.19 (t J 7 3H), 2.30 (s 3H), 2.61 (m 4H), 3.10-3.30 (m 4H), 3.92 (s 6H), 3.97 (s 2H), 4.10 (q J 7 2H), 7.19 (s 1H), 7.91 (s 1H). The ester (0.186 g, 0.50 mmol) is dissolved in ethanol (20 ml), treated with 2M sodium hydroxide (3 ml) and stirred at room temperature overnight. After adjustment to pH 1 with concentrated hydrochloric acid, the solvent is evaporated and the crude acid used directly for formation of the xanthine derivative.

Intermediate 29

N-Chlorosuccinimide (0.347 g, 2.60 mmol) is added to a solution of 6-methoxyisoquinoline (Synth. Commun. 1999, 29, 1617) (0.207 g, 1.30 mmol) in acetic acid (9 ml). The reaction is heated at 50° C. for 3 hours, cooled to ambient temperature, evaporated and partitioned between ethyl acetate and 1M aqueous sodium hydroxide. The organic phase is washed with water and brine, dried over magnesium sulfate and evaporated afford 5-chloro-6-methoxyisoquinoline, $[MH]^+$ 194. A solution of this intermediate (0.175 g, 0.90 mmol) in THF (4.5 ml) and acetic anhydride (0.101 ml, 1.08 mmol) is treated with sodium triacetoxyborohydride (0.229 g, 1.08 mmol) and the reaction is stirred at ambient temperature for 22 hours. The solvent is evaporated, the residue is taken into ethyl acetate, washed with 0.5 M aqueous hydrochloric acid, then brine and dried over magnesium sulfate. Evaporation affords 1-(5-chloro-6-methoxy-1H-isoquinolin-2-yl)-ethanone, mp 78-80° C. A suspension of this intermediate (0.150 g, 0.60 mmol) and glyoxylic acid (76 mg, 0.80 mmol) in 6M aqueous hydrochloric acid (2.8 ml) is heated at 100° C. for 3 hours. After cooling to ambient temperature, the resultant solid is, collected by filtration to afford (5-chloro-6-methoxy-isoquinolin-4-yl)-acetic acid, $[MH]^+$ 252. A suspension of this intermediate (0.970 g, 3.38 mmol) and ammonium formate (1.05 g, 16.9 mmol) in 1:1 acetic acid-water (25 ml) is treated with 10% Pd/C (0.730 g) and stirred at ambient temperature for 16 hours. After filtration through Celite®, the combined filtrate and washings are evaporated and purified by Soxhilet extraction with acetone to afford (6-methoxy-isoquinolin-4-yl)-acetic acid $[MH]^+$ 218. Alternatively reduction of (5-chloro-6-methoxy-isoquinolin-4-yl)-acetic acid to afford (6-methoxy-isoquinolin-4-yl)-acetic acid is accomplished by stirring a suspension of (5-chloro-6-methoxy-isoquinolin-4-yl)-acetic acid (20 g, 69.4 mmol) in 1 Molar sodium hydroxide solution (400 mL) for 20 min, filtering off the resultant salt and then treating with hydgrogen gas in the presence of 10% Pd/C (1.4 g) at atmospheric pressure for 2.25 h. The resulting suspension is filtered through glass wool and celite, washing with water (50 mL). The solution is then cooled in an ice water bath and slowly (30 min) neutralised and then acidified with 5 Molar hydrochloric acid (80 ml). A suspension forms and further crystalisation is encouraged by standing at 5° C. for 20 h. The resulting crystals are removed by filtration and washed with ice cold ethanol (25 ml) drying under reduced pressure gives (6-methoxy-isoquinolin-4-yl)-acetic acid.

Intermediate 30

Glyoxylic acid (1.37 g, 9.28 mmol) is added to mixture of 1-(6-chloro-1H-isoquinolin-2yl)-ethanone [J. Org. Chem., 1980, 45, 1950] (1.44 g, 5.90 mmol) in 6N HCl (24 ml). The reaction is heated at 100° C. for 3 hours, cooled to RT, washed with ether and evaporated to 10 ml volume. After overnight refrigeration, the solid is collected by filtration and dried to afford (6-chloro-isoquinolin-4-yl)-acetic acid hydrochloride. $^1$H NMR (400 MHz, DMSO) δ: 4.45 (s 2H), 8.18 (d J 9 1H), 8.52 (s 1H), 8.70 (d J 8 1H), 8.83 (s1H), 9.96 (s 1H).

Intermediate 31

Sodium borohydride (1.12 g, 29.6 mmol) is added portionwise to a cooled (0° C.) solution of 6-bromoisoquinoline [J Chem Soc Perkin Trans 2, 1998, 437] (1.544 g, 7.42 mmol) in acetic acid (10 ml) and acetic anhydride (3 ml). After heating at 60° C. for 4 hours, the mixture is cooled, evaporated and diluted with water. After adjustment to pH10 with potassium carbonate and extraction with ethyl acetate, the combined organic phases are washed twice with 0.5N HCl and brine, then dried over sodium sulphate. Evaporation affords 1-(6-bromo-1H-isoquinolin-2-yl)-ethanone, $MH^+$ 253. Glyoxylic acid (0.812 g, 8.80 mmol) is added to mixture of 1-(6-bromo-1H-isoquinolin-2-yl)-ethanone (1.50 g, 5.90 mmol) in 6N HCl (20 ml). The reaction is heated at 100° C. for 2 hours, cooled to RT and washed with ethyl acetate. After evaporation, the residue is taken into methanol (20 ml), concentrated sulphuric acid (10 drops) is added and the mixture heated at reflux for 14 hours. After partial evaporation of the solvent, the resultant solid is collected by filtration, washed with methanol and dried to afford (6-bromo-isoquinolin-4-yl)-acetic acid methyl ester hydrochloride, $MH^+$ 281. Lithium hydroxide hydrate (8.5 mg, 0.20 mmol) is added to a cooled (0° C.) solution of (6-bromo-isoquinolin-4-yl)-acetic acid methyl ester (50 mg, 0.18 mmol) in 3:1 THF-water (3 ml). After 1 hour the solvent is evaporated to afford (6-bromo-isoquinolin-4-yl)-acid lithium salt, MH$^+$ 266.

Intermediate 32

Trimethylsilylacetylene (0.17 ml, 1.23 mmol) is added to a suspension of (6-bromo-isoquinolin-4-yl)-acetic acid methyl ester (0.325 g, 1.03 mmol) in DMF (1.75 ml) and triethylamine (10 ml), follwed by copper(I) iodide (40 mg, 0.20 mmol) and (Ph$_3$P)$_2$PdCl$_2$ (73 mg, 0.10 mmol). The reaction is heated at 45° C. for 40 minutes, cooled to ambient temperature and diluted with ethyl acetate. After washing with water and brine, the organic phase is dried over, magnesium sulfate, evaporated and purified by flash column chromatography (1:1 ethyl acetate-hexane elution) to afford (6-trimethylsilanylethynyl-isoquinolin-4-yl)-acetic acid methyl ester, [MH]$^+$ 298. This intermediate (0.221 g, 0.74 mmol) is dissolved in methanol (7.5 ml) and treated with potassium carbonate (75 mg, 0.54 mmol). The reaction is stirred for 30 minutes at ambient temperature, evaporated and purified by flash chromatography (5:1 dichloromethane-methanol elution) to afford (6-ethynyl-isoquinolin-4-yl)-acetic acid, [MH]$^+$ 212.

Intermediate 33

Bromine (0.211 mi, 6.28 mmol) in dichloromethane (10 ml) is added to a cooled (0° C.) solution of 6-methoxyisoquinoline [Synth. Commun. 1999, 29, 1617] and the reaction is stirred at ambient temperature for 20 hours. After pouring into 1M aqueous sodium hydroxide, the organic phase is washed with brine, dried over magnesium sulfate and evaporated. The crude product is purified by flash column chromatography (20:1 dichloromethane-methanol elution) to afford 5-bromo-6-methoxyisoquinoline, [MH]$^+$ 240. This material is then converted according to the procedure for Intermediate 29 into (5-bromo-6-methoxy-isoquinolin4-yl)-acetic acid [MH]$^+$ 298.

Intermediate 34

[1-(3,5-Diisopropoxy-phenyl)-6,7-dimethoxy-isoquinolin-4-yl]-acetic acid is prepared using the general procedure for Intermediate 20, $^1$H NMR (400 MHz CDCl$_3$) δ 1.25 (d J 6 12H), 3.78 (s 3H), 3.86 (s 2H), 3.92 (s 3H), 6.46 (d J 0.5 1H), 6.65 (d J 0.5 2H), 7.20 (s 2H), 8.30 (s 1H).

The following are prepared analogously to Intermediate 21:

Intermediate 35: 1-(3,5-Dimethoxy-phenyl)-6-isopropoxy-7-methoxy-isoquinolin-4-yl]-acetic acid, [MH]$^+$ 412.

Intermediate 36: (1-.tert.-Butyl-6-isopropoxy-7-methoxy-isoquinolin-4-yl)-acetic acid, $^1$H NMR (400 MHz, CDCl$_3$) δ 1.32 (d J 7 6H), 1.52 (s 9H), 3.80 (s 2H), 3.90 (s 3H), 4.75 (heptet J 7 1H), 7.28 (s 1H), 7.66 (s 1H), 8.08 (s 1H).

Intermediate 37: (6-Isopropoxy-1-isopropyl-7-methoxy-isoquinolin-4-yl)-acetic acid, [MH]$^+$ 318.

The following are prepared analogously to Intermediate 20:

Intermediate 38: (6,7-Dimethoxy-1-methyl-isoquinolin-4-yl)acetic acid, [MH]$^+$ 262.

Intermediate 39: (1-tert.-Butyl-6,7-dimethoxy-isoquinolin-4-yl)-acetic acid, $^1$H NMR (400 MHz, CDCl$_3$) d 1.75 (s 9H), 3.95 (s 6H), 4.04 (s 2H), 7.28 (s 1H), 7.75 (s 1H), 8.66 (s 1H).

Intermediate 40: (1-Isopropyl-6,7-dimethoxy-isoquinolin-4-yl)-acetic acid, characterised as the ethyl ester $^1$H NMR (400 MHz, CDCl$_3$) δ 1.25 (t J 7 3H), 1.45 (d J 7 3H), 3.82 (heptet J 7 1H), 3.90 (s 2H), 3.08 (s 2H), 4.15 (q J 7 2H), 7.28 (s 1H), 7.48 (s 1H), 8.30 (s 1H).

Intermediate 41: 2-(7Methoxy-1-morpholin-4-yl-isoquinolin4-yl)-propionic acid mp 225-227° C., is prepared according to the procedure for Intermediate 27.

The following are prepared analogously to Intermediate 22:

Intermediate 42: [MH]$^+$ 332 (7-Hydroxy-6-methoxy-isoquinolin-4-yl)-acetic acid lithium salt, via (3-benzyloxy-4-methoxy-benzyl)-(2,2-dimethoxy-ethyl)-amine.

Intermediate 43: (6,7-Dimethoxy-3-methyl-isoquinolin-4-yl)-acetic acid, $^1$H NMR (400 MHz, DMSO) δ: 2.50 (s 3H), 3.91 (s 3H), 3.93 (s 3H), 4.02 (s 2H), 7.30 (s 1H), 7,43 (s 1H), 8.30 (s 1H).

Intermediate 44: (6-Ethoxy-7-methoxy-isoquinolin-4-yl)-acetic acid, 3 M$^+$ 261.

The following are prepared analogously to Intermediate 22, using pyruvic acid in place of glyoxylic acid:

Intermediate 45: 2-(6-Ethoxy-7-methoxy-isoquinolin-4-yl) propionic acid lithium salt, characterised as the methyl ester, M$^+$ 290.

Intermediate 46: 2-(7-Ethoxy-6-methoxy-isoquinolin-4-yl)-propionic acid lithium salt, characterised as the methyl ester, M$^+$ 290.

Intermediate 47: 2-(6,7-dimethoxy-isoquinolin-4-yl)-propionic acid, characterised as the methyl ester, M$^+$ 276.

Intermediate 48: 8-Fluoro-6-methoxy-isoquinolin-4-yl)-acetic acid, is prepared according to the procedure for Intermediate 31 and characterised as the methyl ester, [MH]$^+$ 250.

Intermediate 49: (6,7-dimethoxy-isoquinolin-4-yl)-acetic acid, and Intermediate 50, [1,3]dioxolo[4,5-.g.]isoquinolin-8-yl-acetic acid, are prepared as described in Dyke et al, Tetrahedron 1968,24, 1467.

Intermediate 51: (7-methoxy-isoquinolin-4-yl)-acetic acid is prepared according to Dyke et al, Tetrahedron, 1973,29, 3881.

Intermediate 52: 2,2-Dimethoxyethylamine (13.85 ml, 0.13 mol) is added to a solution of 3-fluoro-4-methoxybenzaldehyde (20 g, 0.13 mol) in toluene (200 ml). The resulting solution is flushed with nitrogen gas and then heated overnight under reflux in a Dean-Stark apparatus. The solvent is then removed under reduced pressure to yield (2,2-dimethoxy-ethyl)-[1-(3-fluoro-4-methoxy-phenyl)-methylidene]-amine. This intermediate (31 g, 0.13 mol) is dissolved in ethylacetate and acetic anhydride (13.1 g, 0.13 mol) added. Platinum oxide (0.3 g) is then added, under a blanket of nitrogen, and the resulting mixture is stirred under a hydrogen atmosphere until uptake is complete. Filtration, washing with saturated aqueous NaHCO$_3$ (3×100 ml), brine and water, drying over MgSO$_4$ and concentration then gives N-(2,2-dimethoxy-ethyl)-N-(3-fluoro-4-methoxy-benzyl)-acetamide. This intermediate (38.9 g, ca 0.13 mol) is dissolved in anhydrous CH$_2$Cl$_2$ and then added slowly over 20 mins to a stirred mixture of AlCl$_3$ (90 g) and CH$_2$Cl$_2$ under an atmosphere of nitrogen. The total volume of CH$_2$Cl$_2$ is 250 ml. The mixture is stirred for a further 10 mins at room temperature and is then cooled with an ice bath during the addition of aqueous 40% NaOH. The mixture is further diluted with water (250 ml), filtered through glass wool, the organic phase separated and the aqueous phase further extracted with CH$_2$Cl$_2$ (2×200 ml). Drying over MgSO$_4$ and evaporation under reduced pressure yields a crude oil which is purified by flash silica chromatography (eluant: 1% methanol in CH$_2$Cl$_2$) to give as one of the products 1-(7-fluoro-6-methoxy-1H-isoquinolin-2-yl)-ethanone. This intermediate (0.60 g, 2.7 mmol) is mixed with glyoxylic acid (0.325 g, 3.5 mmol) and water (10 ml) and the resulting mixture is stirred at room temperature for 20 min. Concentrated hydrochloric acid (10 ml) is then added and the mixture heated to reflux for 1 h. Concentration and purification by preparative HPLC gives (7-fluoro-6-methoxy-isoquinolin-4-yll)-acetic acid, [MH]$^+$ 236.

The following are prepared analogously to Intermediate 20:

Intermediate 53: (1-Methyl-6-methoxy-isoquinolin-4-yl)-acetic acid.

Intermediate 54: (6-Isopropoxy-1-methyl-isoquinolin-4-yl)-acetic acid.

Intermediate 55: (6-Ethoxy-1-methyl-isoquinolin-4-yl)-acetic acid.

Intermediate 56: A solution of (6-bromo-isoquinolin-4-yl)-acetic acid methyl ester (52 mg, 0.19 mmol), prepared as described as an intermediate for Intermediate 31, in DMF (3 ml) is added to zinc dicyanide (26 mg, 0.2 mmol) under a nitrogen atmosphere. To the resulting mixture is added 1,1'-bis(diphenylphosphino)ferrocene (15 mg) and tris(dibenzylideneacetone)dipalladium(0) (8 mg) and the resulting mixture stirred at 120° C. for 22 h. The solution is cooled and diluted with chloroform (30 ml) and washed with water (2×20 ml) followed by brine (20 ml). Further chloroform is added (40 ml) and the solution dried over MgSO$_4$, filtered and concentrated. Repetitive flash silica column chromatography (eluants 40:1 CH$_2$Cl$_2$:methanol, then 50:1 CH$_2$Cl$_2$:methanol) gives (6-cyano-isoquinolin-4-yl)-acetic acid methyl ester [MH]$^+$ 227. This intermediate is saponified by treatment with LiOH in 3:1 THF/water. The resulting mixture is partially evaporated to remove the THF, diluted to 10 ml with water then washed with ethyl acetate. The aqueous phase is then neutralised with 1M hydrochloric acid (to pH 4-5) and exhaustively extracted with ethylacetate. The organic phase is dried over MgSO$_4$, filtered and concentrated to give (6-cyan-isoquinolin-4-yl)-acetic acid M$^+$ 212.

Intermediate 57: (5-Chloro-6-methoxy-isoquinolin-4-yl)-acetic acid is prepared as described in the procedure for intermediate 29.

Intermediate 58: To a solution of (6-trimethylsilanylethynyl-isoquinolin-4-yl)-acetic acid methyl ester, as prepared for Intermediate 32 (0.19 g, 0.64 mmol), in anhydrous methanol (7 ml) is added K$_2$CO$_3$ (72 mg) and the resulting mixture stirred for, 1 h. Additional K$_2$CO$_3$ (11 mg) is then added and stirring continued for 30 min. The mixture is then neutralised with glacial acetic acid and concentrated. Purification by flash silica column chromatography (ethylacetate/hexane 1:1) gives (6-ethynyl-isoquinolin-4-yl)-acetic acid methyl ester M$^+$ 225. This intermediate (79 mg, 0.35 mmol) is dissolved in methanol under an inert atmosphere and 10% Pd on carbon (79 mg) added. The resulting suspension is stirred vigorously under an atmosphere of gaseous hydrogen. After 90 mins, filtration, washing with methanol and concentration give (6-ethyl-isoquinolin-4-yl)-acetic acid methyl ester M$^+$ 229. To a solution of this intermediate (68 mg, 0.30 mmol) in THF/methanol/water (3:1:1, 3.5 ml) is added LiOH (12.5 mg) and the mixture stirred for 20 h at room temperature. Concentration under reduced pressure gives lithium (6-ethyl-isoquinolin-4-yl)-acetate M$^+$ 221.

Intermediate 59: A solution of Intermediate 29 (0.5 g, 2.3 mmol) is suspended in aqueous 48% HBr (10 ml) and then heated at 100° C. for 48 h. Further aqueous 48% HBr (10 ml) is then added and heating continued at 100° C. for an additional 24 h. The reaction mixture is cooled to 5° C. for 4 h and the resulting solid separated by filtration. Washing with water and drying under high vacuum at 50° C. gives (6-hydroxy-isoquinolin-4-yl)-acetic acid hydrobromide [MH]$^+$ 204.4. This intermediate (0.15 g, 0.53 mmol) is suspended in DMF (2 ml) and K$_2$CO$_3$ (0.22 g, 1.58 mmol) added followed by ethyliodide (0.085 ml, 1.06 mmol) and the resulting mixture stirred at room temperature for 2 h. Concentration and purification by flash silica column chromatography (eluant: CH$_2$Cl$_2$/methanol 10:1) gives (6-ethoxy-isoquinolin-4-yl)-acetic acid ethyl ester [MH]$^+$ 260. This intermediate (25 mg, 0.11 mmol) is dissolved in water (1 ml) and LiOH added (5 mg, 0.11 mmol). The resulting mixture is stirred for 30 min at room temperature. Acidification with minimum 6N HCl and concentration gives crude (6-ethoxy-isoquinolin-4-yl)acetic acid.

EXAMPLES 1-70

Compounds of formula I which are also of formula

XXXXVI

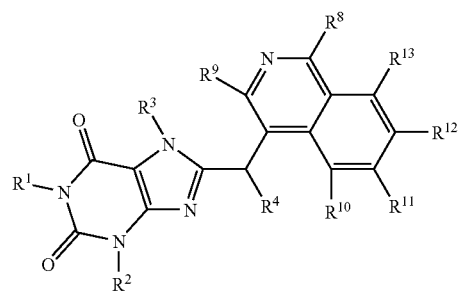

where R$^1$ to R$^4$ and R$^8$ to R$^{13}$ are as hereinbefore defined, in free or salt form, and their methods of preparation are shown in the following table, the methods being described hereinafter. R$^3$ is H in all Examples except No 44, where it is CH$_3$. R$^4$ is H in all examples except Nos 25-27 and 41-43, where it is CH$_3$. R$^9$ is H in all Examples except No 29, where it is CH$_3$. R$^{10}$ is H in all Examples except No 57, where it is Br and No 75 where it is Cl. R$^{13}$ is H in all Examples except Nos 56 where it is F, and 65 and 66, where it is Br.

| Ex. No. | R¹ | R² | R⁸ | R¹¹ | R¹² | m/z MH+ | MH− | Method | Reacting Intermediates |
|---|---|---|---|---|---|---|---|---|---|
| 1 | $CH_3$ | $(CH_3)_2CHCH_2$ | 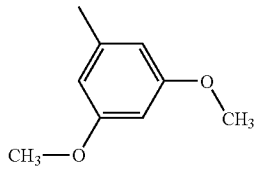 | $OCH_3$ | $OCH_3$ | 560 | | A | 11 + 20 |
| 2 | $CH_3$ | $(CH_3)_2CHCH_2$ | 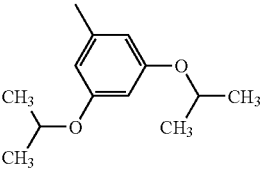 | $OCH_3$ | $OCH_3$ | 616 | | A | 11 + 34 |
| 3 | $CH_3$ | $(CH_3)_2CHCH_2$ | 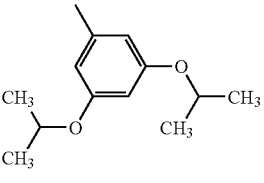 | $OCH(CH_3)_2$ | $OCH_3$ | 644 | | A | 11 + 21 |
| 4 | $CH_3$ | $(CH_3)_2CHCH_2$ | 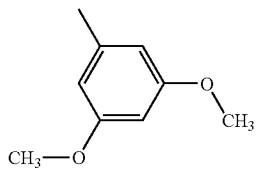 | $OCH(CH_3)_2$ | $OCH_3$ | 588 | | A | 11 + 35 |
| 5 | $CH_3$ | $(CH_3)_2CHCH_2$ | $(CH_3)_3C$ | $OCH(CH_3)_2$ | $OCH_3$ | 508 | | A | 11 + 36 |
| 6 | $CH_3$ | $(CH_3)_2CHCH_2$ | $(CH_3)_2CH$ | $OCH(CH_3)_2$ | $OCH_3$ | 494 | | A | 11 + 37 |
| 7 | $CH_3$ | $(CH_3)_2CHCH_2$ | $CH_3$ | $OCH_3$ | $OCH_3$ | 437 (M+) | | A | 11 + 38 |
| 8 | $CH_3$ | $(CH_3)_2CHCH_2$ | $(CH_3)_3C$ | $OCH_3$ | $OCH_3$ | 480 | | A | 11 + 39 |
| 9 | $CH_3$ | $(CH_3)_2CHCH_2$ | $(CH_3)_2CH$ | $OCH_3$ | $OCH_3$ | 465 (M+) | | A | 11 + 40 |
| 10 | $CH_3$ | $(CH_3)_2CHCH_2$ | H | $OCH_3$ | $OCH_3$ | 424 | | C | 11 + 49 |
| 11 | $CH_3$ | 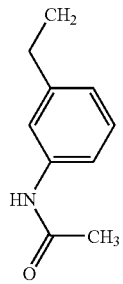 | H | $OCH_3$ | $OCH_3$ | | 513 | A | 2 + 49 |
| 12 | H | $CH_3$ | H | $OCH_3$ | $OCH_3$ | | | C | 12 + 49 |
| 13 | $CH_3$ | $CH_2=CHCH_2$ | H | $OCH_3$ | $OCH_3$ | | | C | 13 + 49 |
| 14 | $CH_3$ | 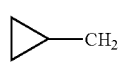 | H | $OCH_3$ | $OCH_3$ | | | C | 14 + 49 |
| 15 | $CH_3$ | $(CH_3)_3CCH_2$ | H | $OCH_3$ | $OCH_3$ | | | C | 15 + 49 |
| 16 | $(CH_3)_2CHCH_2$ | $(CH_3)_2CHCH_2$ | H | $OCH_3$ | $OCH_3$ | | | C | 16 + 49 |

-continued

| Ex. No. | R$^1$ | R$^2$ | R$^8$ | R$^{11}$ | R$^{12}$ | m/z MH+ | m/z MH− | Method | Reacting Intermediates |
|---|---|---|---|---|---|---|---|---|---|
| 17 | CH$_3$ | cyclohexyl-CH$_2$ | H | OCH$_3$ | OCH$_3$ | | | C | 17 + 49 |
| 18 | CH$_3$ | CH$_2$=C(CH$_3$)CH$_2$ | H | OCH$_3$ | OCH$_3$ | | | C | 1 + 49 |
| 19 | CH$_3$ | (tetrahydrofuran-2-yl)CH$_2$ | H | OCH$_3$ | OCH$_3$ | | | C | 5 + 49 |
| 20 | CH$_3$ | CH$_3$CH$_2$CH(CH$_3$)CH$_2$ | H | OCH$_3$ | OCH$_3$ | | | C | 6 + 49 |
| 21 | H | CH$_3$CH$_2$CH$_2$ | H | OCH$_3$ | OCH$_3$ | | | C | 18 + 49 |
| 22 | CH$_3$ | 4-(CH$_3$C(O)NH)-C$_6$H$_4$-CH$_2$ | H | OCH$_3$ | OCH$_3$ | | 515 | C | 3 + 49 |
| 23 | CH$_3$ | (CH$_3$)$_2$CHCH$_2$ | H | 1,3-dioxolan-2-yl | | | | C | 11 + 50 |
| 24 | CH$_3$ | (CH$_3$)$_2$CHCH$_2$ | H | H | OCH$_3$ | 394 | | C | 11 + 51 |
| 25 | CH$_3$ | (CH$_3$)$_2$CHCH$_2$ | Cl | H | OCH$_3$ | 442 | | C | 11 + 24 |
| 26 | CH$_3$ | (CH$_3$)$_2$CHCH$_2$ | CN | H | OCH$_3$ | 433 | | C | 11 + 25 |
| 27 | CH$_3$ | (CH$_3$)$_2$CHCH$_2$ | 4-methylmorpholin-? | H | OCH$_3$ | 493 | | C | 11 + 41 |
| 28 | CH$_3$ | (CH$_3$)$_2$CHCH$_2$ | H | OCH$_3$ | OH | 410.7 | | D | 11 + 42 |
| 29 | CH$_3$ | (CH$_3$)$_2$CHCH$_2$ | H | OCH$_3$ | OCH$_3$ | 438.6 | | D | 11 + 43 |
| 30 | CH$_3$ | CH$_3$(CH$_2$)$_5$ | H | OCH$_3$ | OCH$_3$ | 452.8 | | D | 7 + 49 |
| 31 | CH$_3$ | 3,4-(CH$_3$O)$_2$-C$_6$H$_3$-CH$_2$ | H | OCH$_3$ | OCH$_3$ | 518.4 | | D | 8 + 49 |

-continued

| Ex. No. | R¹ | R² | R⁸ | R¹¹ | R¹² | m/z MH+ | MH− | Method | Reacting Intermediates |
|---|---|---|---|---|---|---|---|---|---|
| 32 | $CH_3$ | $CH_2$-(1,3-benzodioxol-5-yl) | H | $OCH_3$ | $OCH_3$ | 502.4 | | D | 9 + 49 |
| 33 | $CH_3$ | $CH_2$-(2,4-dichlorophenyl) | H | $OCH_3$ | $OCH_3$ | 527.8 | | D | 10 + 49 |
| 34 | $CH_3$ | $CH_2$-(4-methoxyphenyl) | H | $OCH_3$ | $OCH_3$ | 487.9 | | D | 19 + 49 |
| 35 | $CH_3$ | $(CH_3)_2CHCH_2$ | Cl | $OCH_3$ | $OCH_3$ | 458.4 | | D | 11 + 23 |
| 36 | $CH_3$ | $(CH_3)_2CHCH_2$ | H | H | H | 364 | | C | 11 + 26 |
| 37 | $CH_3$ | $(CH_3)_2CHCH_2$ | H | $OCH_2CH_3$ | $OCH_3$ | 438 | | C | 11 + 44 |
| 38 | $CH_3$ | $(CH_3)_2CHCH_2$ | N-morpholinyl | $OCH_3$ | $OCH_3$ | 509.1 | | D | 11 + 27 |
| 39 | $CH_3$ | $(CH_3)_2CHCH_2$ | 4-methylpiperazin-1-yl | $OCH_3$ | $OCH_3$ | 522.02 | | D | 11 + 28 |
| 40 | $CH_3$ | $(CH_3)_2CHCH_2$ | H | $OCH_3$ | $OCH_2CH_3$ | 438 | | C | 11 + 22 |
| 41 | $CH_3$ | $(CH_3)_2CHCH_2$ | H | $OCH_2CH_3$ | $OCH_3$ | 452 | | C | 11 + 45 |
| 42 | $CH_3$ | $(CH_3)_2CHCH_2$ | H | $OCH_3$ | $OCH_2CH_3$ | 452 | | C | 11 + 46 |
| 43 | $CH_3$ | $(CH_3)_2CHCH_2$ | H | $OCH_3$ | $OCH_3$ | 438 | | C | 11 + 47 |
| 44 | $CH_3$ | $(CH_3)_2CHCH_2$ | H | $OCH_3$ | $OCH_3$ | 438 | | J | — |
| 45 | $CH_3$ | $(CH_3)_2CHCH_2$ | H | $OCH_3$ | H | 394 | | B2 | 11 + 29 |
| 46 | $CH_3$ | $CH_3CH_2CH(CH_3)CH_2$ | H | $OCH_3$ | H | 408 | | C | 6 + 29 |
| 47 | $CH_3$ | $(CH_3)_3CCH_2$ | H | Cl | H | | 410 | C | 15 + 30 |
| 48 | $CH_3$ | $(CH_3)_2CHCH_2$ | H | Cl | H | | 396 | C | 11 + 30 |
| 49 | $CH_3$ | cyclopropyl-$CH_2$ | H | $OCH_3$ | H | | | C | 14 + 29 |
| 50 | $CH_3$ | cyclopropyl-$CH_2$ | H | Cl | H | 394 | | C | 14 + 30 |

-continued

| Ex. No. | R¹ | R² | R⁸ | R¹¹ | R¹² | m/z MH+ | m/z MH− | Method | Reacting Intermediates |
|---|---|---|---|---|---|---|---|---|---|
| 51 | $CH_3$ | cyclobutyl-$CH_2$ | H | $OCH_3$ | $OCH_3$ | 436.6 | 434.5 | B1 | 4 + 49 |
| 52 | $CH_3$ | $CH_2=C(CH_3)CH_2$ | H | $OCH_3$ | H | 392 | 390 | C | 1 + 29 |
| 53 | $CH_3$ | $(CH_3)_2CHCH_2$ | H | Br | H | 441 | | C | 11 + 31 |
| 54 | $CH_3$ | $(CH_3)_3CCH_2$ | H | $OCH_3$ | H | 408 | | C | 15 + 29 |
| 55 | $CH_3$ | $(CH_3)_2CHCH_2$ | H | C≡CH | H | 388 | | B1 | 11 + 32 |
| 56 | $CH_3$ | $(CH_3)_2CHCH_2$ | H | $OCH_3$ | H | 412 | | C | 11 + 48 |
| 57 | $CH_3$ | $(CH_3)_2CHCH_2$ | H | $OCH_3$ | H | 473 | | C | 11 + 33 |
| 58 | $CH_3$ | 3-aminophenyl-ethyl | H | $OCH_3$ | $OCH_3$ | | | E | — |
| 59 | $CH_3$ | 3-(N,N-dimethylsulfamoylamino)phenyl-ethyl | H | $OCH_3$ | $OCH_3$ | | | F | — |
| 60 | $CH_3$ | 4-(N,N-dimethylsulfamoylamino)phenyl-ethyl | H | $OCH_3$ | $OCH_3$ | 580 | | F | — |
| 61 | $CH_3$ | 4-(isopropylsulfonylamino)phenyl-ethyl | H | $OCH_3$ | $OCH_3$ | 578 (M+) | | F | — |
| 62 | $CH_3$ | 4-aminophenyl-ethyl | H | $OCH_3$ | $OCH_3$ | 473 | | E | — |
| 63 | $CH_3$ | $(CH_3)_2CHCH_2$ | H | H | OH | 379 | | G | — |
| 64 | $CH_3$ | $(CH_3)_2CHCH_2$ | H | OH | OH | 396 | | G | — |
| 65 | $CH_3$ | $(CH_3)_2CHCH_2$ | H | OH | OH | 474 | | H | — |
| 66 | $CH_3$ | $(CH_3)_2CHCH_2$ | H | H | OH | | | H | — |
| 67 | $CH_3$ | $HO(CH_2)_3$ | H | $OCH_3$ | $OCH_3$ | 426 | | I | — |
| 68 | $CH_3$ | $HOCH_2CH(CH_3)CH_2CH_3$ | H | $OCH_3$ | $OCH_3$ | 440 | | I | — |

-continued

| Ex. No. | R¹ | R² | R⁸ | R¹¹ | R¹² | m/z MH+ | MH− | Method | Reacting Intermediates |
|---|---|---|---|---|---|---|---|---|---|
| 69 | CH₃ | 2-methylbutyl acetate (CH₃CH₂CH(CH₃)CH₂OC(O)CH₃) | H | OCH₃ | OCH₃ | 482 | | K | — |
| 70 | CH₃ | 1-ethyl-1-methylcyclopropyl | H | OCH₃ | OCH₃ | 436 | | L | — |
| 71 | CH₃ | cyclohexylmethyl (C₆H₁₁CH₂) | H | OCH₃ | H | 434 | | B1 | 17 + 29 |
| 72 | CH₃ | (tetrahydrofuran-2-yl)methyl | H | OCH₃ | H | 422 | | B1 | 5 + 29 |
| 73 | CH₃ | (CH₃)₂CHCH₂ | H | OCH₃ | F | 412 | 410 | B1 | 11 + 52 |
| 74 | CH₃ | (CH₃)₂CHCH₂ | H | CO₂H | H | 408 | | C | 11 + 56 |
| 75 | CH₃ | (CH₃)₂CHCH₂ | H | OCH₃ | H | 428 | | B1 | 11 + 57 |
| 76 | CH₃ | (CH₃)₂CHCH₂ | H | CN | H | 389 | | M | |
| 77 | CH₃ | (CH₃)₂CHCH₂ | H | CH₂CH₃ | H | 392 | | B1 | 11 + 58 |
| 78 | CH₃ | (CH₃)₂CHCH₂ | H | OCH₂CH₃ | H | 408.54 | | B1 | 11 + 59 |
| 79 | CH₃ | 4-amino-phenylethyl (4-H₂N-C₆H₄-CH₂CH₂-) | H | OCH₃ | H | 443.44 | | B1 + E | 3 + 29 |
| 80 | CH₃ | 4-(isopropylsulfonylamino)phenylethyl | H | OCH₃ | H | 549 | 547 | F | |
| 81 | CH₃ | 4-(N,N-dimethylsulfamoylamino)phenylethyl | H | OCH₃ | H | 549 M⁺ | | F | |
| 82 | CH₃ | (CH₃)₂CHCH₂ | N(CH₂)₃ | OCH₃ | OCH₃ | 467 | 465 | N | 11 + 23 |
| 83 | CH₃ | (CH₃)₂CHCH₂ | N-methylpiperidinyl | OCH₃ | OCH₃ | 507 | 505 | O | 11 + 23 |
| 83 | CH₃ | (CH₃)₂CHCH₂ | CH₃ | OCH₃ | H | 408 | 406 | A | 11 + 53 |
| 84 | CH₃ | (CH₃)₂CHCH₂ | CH₃ | OCH(CH₃)₂ | H | M⁺ 435 | | A | 11 + 54 |
| 85 | CH₃ | (CH₃)₂CHCH₂ | CH₃ | OCH₂CH₃ | H | 422 | 420 | A | 11 + 55 |

Method A 1-(3-Dimethylaminopropyl)-3-ethylcarbodiimide hydrochloride (0.201 g, 1.30 mmol) is added to 5,6-diamino-1-isobutyl-3-methyl-1H-pyrimidine-2,4-dione (0.223 g, 1.05 mmol)) and (6,7-dimethoxy-1-methyl-isoquinolin-4-yl)-acetic acid (0.25 g, 0.96 mmol) in methanol (5 ml) and water (1 ml) and the mixture is stirred at ambient temperature for 16 hours. The methanol is evaporated and the resultant solid collected by filtration, taken into methanol (5 ml) and 5M aqueous sodium hydroxide (0.5 ml) is added. The reaction is heated to reflux for 1 hour, cooled to ambient temperature and evaporated. The residue is dissolved in water and extracted with dichloromethane, the combined organic extracts are dried over sodium sulfate and evaporated to afford 8-(6,7-dimethoxy-1-methyl-isoquinolin-4-ylmethyl)-3-isobutyl-1-methyl-3,7-dihydro-purine-2,6-dione, $M^+$ 437.

Method B1

(6-Ethynyl-isoquinolin-4-yl)-acetic acid (58 mg, 0.28 mmol) is dissolved in DMF (1 ml) and O-(7-azabenzotriazo-1-yl)-N,N,N',N'-tetramethyluronium hexafluorophosphate (0.125 g, 0.33 mmol) and Hunig's base (0.180 ml, 1.03 mmol) are added, followed by a solution of 5,6-diamino-1-isobutyl-3-methyl-1H-pyrimidine-2,4-dione (58 mg, 0.28 mmol) in DMF (0.7 ml). The reaction is stirred at room temperature for 2 hours. The solvent is evaporated and the residue purified by flash column chromatography (30:1 dichloromethane-methanol elution). The intermediate is dissolved in methanol (2 ml) and water (2.75 ml) added, followed by 4M aqueous sodium hydroxide (0.25 ml). The reaction is heated at 40° C. for 2 hours, then stirred for 16 hours at ambient temperature. The solvent is evaporated and the crude product purified by flash column chromatography (30:1 dichloromethane-methanol elution) to afford 8-(6-ethynyl-isoquinolin-4-ylmethyl)-3-isobutyl-methyl-3,7dihydro-purine-2,6-dione, $[MH]^+$ 388.

Method B2

A suspension of (6-methoxy-isoquinolin-4-yl)-acetic acid (3.5 g, 13.82 mmol) in acetonitrile (70 ml) is treated sequentially with Hunig's base (6.15 ml, 36 mmol), O(7-benzotriazo-1-yl)-N,N,N', N'-tetramethyluronium hexafluorophosphate (6.29 g, 16.6 mmol) and 5,6-diamino-1-isobutyl-3-methyl-1H-pyrimidine-2,4-dione (3.22 g, 15.2 at mmol) while the solution is stirred at room temperature. The reaction is stirred at ambient temperature for 2 h, prior to evaporation of the solvent. The residue is triturated with ethyl acetate (50 ml) filtered and washed with ethyl acetate and then dried at 50° C. under reduced pressure. The resulting intermediate is suspended in a mixture of methanol (30 ml) and 4M aqueous sodium hydroxide (60 ml) and heated at 80° C. for 45 minutes. This suspension is neutralised with acetic acid and cooled to 0-5° C. overnight. The resultant solid is collected by filtration, and washed with methanol/water 1:9 (30 ml) followed by methanol (30 ml). Drying under high vacuum at 50° C. affords 3-isobutyl-8-(6-methoxy-isoquinolin-4-ylmethyl)-1-methyl-3,7-dihydro-purine-2,6-dione, $[MH]^+$ 394.5.

Method C 1-(3-Dimethylaminopropyl)-3-ethylcarbodiimide hydrochloride (5.6M aqueous solution, 0.33 ml, 1.85 mmol) is added to a suspension of 5,6-diamino-1-isobutyl-3-methyl-1H-pyrimidine-2,4-dione (0.327 g, 1.54 mmol), (1-chloro-6,7-dimethoxy-isoquinolin-4-yl)-acetic acid (0.414 g, 1.54 mmol) and 1-hydroxybenzotriazole (0.251 g, 1.85 mmol) in $CH_2Cl_2$ (2 ml). Water (2 ml) is added, the biphasic mixture is shaken for 18 hours and the the resultant solid is collected by filtration. This intermediate is suspended in methanol (10 ml), 4M aqueous NaOH (5 ml) is added and the mixture heated to reflux for 4 hours. After evaporation of the methanol, the residue is acidified to pH2 with concentrated hydrochloric acid and the resultant solid collected by filtration and purified by preparative HPLC to afford 8(1-chloro-6,7-dimethoxy-isoquinolin-4-ylmethyl)-3-isobutyl-1-methyl-3,7-dihydro-purine-2,6-dione hydrochloride, $[M]^+$ 458.

Method D 1-(3-Dimethylaminopropyl)-3-ethylcarbodiimide (20.6 ml, 0.1 mol) is added to a mixture of 5,6-diamino-1-isobutyl-3-methyl-1H-pyrimidine-2,4-dione (20 g, 0.094 mol), (5,6-dimethoxy-isoquinolin-4-yl)-acetic acid (26.7 g, 0.094 mol), and 1-hydroxybenzotriazole (19.2 g, 0.142 mol) in 1:1 dichloromethane-water (400 ml). The reaction is stirred at ambient temperature for 4.5 hours and the resultant solid collected by filtration. Slurrying in water (500 ml), filtration and washing with water (250 ml) followed by drying, further trituration with methanol and drying gives an intermediate together with slightly less pure material from concentration of the methanol triturate. The intermediate (16.08 g) is dissolved in water (100 ml) and methanol (100 ml) followed by the addition of 4M aqueous sodium hydroxide (56 ml) and the resultant solution is heated at 70° C. over night. After cooling to ambient temperature, the methanol is evaporated and the residue acidified to pH 1 with concentrated hydrochloric acid. The resultant hydrochloride salt is collected by filtration and dried. The product is then be converted to the free base by treatment with aqueous sodium hydroxide to pH 11 and washing with water to afford 3-isobutyl-8-(5,6-dimethoxy-isoquinolin-4-ylmethyl)-1-methyl-3,7-dihydro-purine-2,6-dione $[MH]^+$ 424.6.

Method E

A suspension of the product of Example 11 (72 mg, 0.13 mmol) in 6N HCl (25 ml) and ethanol (1.5 ml) is heated to reflux for 5 hours then stood at room temperature overnight. The resultant precipitate is collected by filtration, washed with water and dried to afford 3-(3-amino-benzyl)8-(6,7-dimethoxy-isoquinolin-4- ylmethyl)-1-methyl-3,7-dihydro-purine-2,6-dione dihydrochloride, $^1$H NMR (400 MHz, DMSO) δ: 3.20 (s 3H), 3.95 (s 3H), 4.00 (s 3H), 4.75 (s 2H), 5.15 (s 2H), 7.15 (m 2H), 7.20 (s 1H), 7.30 (t J 6 1H), 7.65 (s 1H), 7.95 (s 1H), 8.50 (s 1H), 9.50 (s 1H), 13.6 (br s 1H).

Method F

The product of Example 58 (37 mg, 0.07 mmol) is suspended in pyridine (1.5 ml) and dimethylsulfarmoyl chloride (23 ml, 0.21 mmol) is added. The reaction is heated at 50° C. for 22 hours and the solvent is evaporated. Trituration with water gives a solid which is collected by filtration and dried to afford 3-[3-(N,N-dimethylsulfarmoyl) aminobenzyl]-8-(6,7-dimethoxy-isoquinolin-4-ylmethyl)-1-methyl-3,7-dihydro-purine-2,6-dione, $^1$H NMR (400 MHz, DMSO) δ: 2.64 (s 6H), 3.26 (s 3H), 3.86 (s 3H), 3.98 (s 3H), 4.50 (s 2H), 5.15 (s 2H), 6.98 (d J 6 1H), 7.08 (d J 6 1H), 7.15 (s 1H), 7.22 (t 6 3H), 7.55 (s 1H), 7.62 (s 1H), 8.38 (s 1H), 9.15 (s 1H), 9.82 (s 1H), 13.60 (s 1H).

Method G

The product of Example 24 (100 mg, 0.25 mmol) is heated at 100° C. in concentrated hydrobromic acid (5 ml) for 36 hours. The solvent is evaporated and the crude product purified by preparative HPLC to afford 8-(7-hydroxy-isoquinolin-4-ylmethyl)-3-isobutyl-1-methyl-3,7-dihydro-purine-2,6-dione, [M]$^+$ 379.

Method H

The product of Example 64 (41 mg, 0.09 mmol) is dissolved in acetic acid (2 ml) and treated with bromine in acetic acid (148 mg/ml solution: 100 μl). After 1 hour at room temperature the solvent is evaporated, the residue dissolved in hot methanol, filtered and evaporated to afford 8-(8-bromo-6,7-dihydroxisoquinolin-4-ylmethyl)3-isobutyl-1-methyl-3,7-dihydro-purine-2,6-dione, M$^+$ 474.

Method I

A suspension of the product of Example 13, 3-allyl-8-(6,7-dimethoxy-isoquinolin-4-ylmethyl)-1-methyl-3,7-dihydro-purine-2,6dione -hydrochloride salt (0.760 g, 1.87 mmol), 9-borabicyclo[2.2.0]nonane (0.5M THF solution, 18.7 ml, 9.35 mmol) and diisopropylethylamine (0.33 ml, 1.89 mmol) in THF (9 ml) is heated to reflux for 2.5 hours. Sodium hydroxide (4M aqueous solution, 6 ml) and hydrogen peroxide (27.5%, 3 ml) are added sequentially and the reaction heated at 50° C. for 1.5 hours. After evaporation, the crude product is purified by flash chromatography (19:1 CH$_2$Cl$_2$:methanol elution) and triturated with water to afford 8-(6,7-dimethoxy-isoquinolin-4-ylmethyl)-3-(3-hydroxy-propyl)-1-methyl-3,7-dihydro-purine-2,6-dione, [MH]$^+$ 426.

Method J

Potassium carbonate (48 mg, 0.35 mmol) and iodomethane (0.018 ml, 0.295 mmol) are added to a solution of the product of Example 10, 8-(6,7-dimethoxy-isoquinolin-4-ylmethyl)-3-isobutyl-1-methyl-3,7-dihydro-purine-2,6-dione (0.100 g, 0.24 mmol) in DMF (2 ml). The reaction is stirred overnight and purified by preparative HPLC to afford 8-(6,7-dimethoxy-isoquinolin-4-ylmethyl)-3-isobutyl-1,7-dimethyl-3,7-dihydro-purine-2,6-dione, [MH]$^+$ 438.

Method K

A suspension of the product of Example 68, 8-(6,7-dimethoxy-isoquinolin-4-ylmethyl)-3-(3-hydroxy-2-methyl-propyl)-1-methyl-3,7-dihydro-purine-2,6-dione (63 mg, 0.144 mmol) and acetyl chloride (18 ml, 0.25 mmol) in pyridine (1 ml) is heated at 50° C. for 18 hours. After evaporation, flash chromatography (19:1 dichloromethane-methanol elution) affords acetic acid 3-[8-(6,7-dimethoxy-isoquinolin-4-ylmethyl)-1-methyl-2,6dioxo-1,2,6,7-tetrahydro-purin-3-yl]-2-methyl-propyl ester, [MH]$^+$ 482.

Method L

The product of Example 18, 8-(6,7-dimethoxy-isoquinolin-4-ylmethyl)-1-methyl-3-(2-methyl-allyl)-3,7-dihydro-purine-2,6-dione (100 mg, 0.24 mmol) is suspended in 1,2-dichloroethane (30 ml). Diethyl zinc (1M hexane solution, 1.2 ml, 1.20 mmol) is added, followed by chloroiodomethane (0.174 ml, 0.24 mmol) and the reaction is stirred at ambient temperature for 1 hour, prior to quenching with saturated aqueous NH$_4$Cl. After extraction with chloroform, the organic, phase is washed with water, dried over MgSO$_4$ and evaporated. Purification by preparative HPLC affords 8-(6,7-methoxy-isoquinolin-4-ylmethyl)-1-methyl-3-(1-methylcyclopropylmethyl)-3,9-dihydro-purine-2,6-dione, [MH]$^+$ 436.

Method M

The product of Example 53, 8-(6-bromo-isoquinolin-4-ylmethyl)-3-isobutyl-1-methyl-3,7-dihydro-purine-2,6-dione (245 mg, 0.554 mmol) is dispersed in a mixture of triethylamine (0.085 ml, 0.61 mmol) and CH$_2$Cl$_2$ (4 ml). To the stirred mixture is added dropwise a solution of di-tert butoxycarbonate (133 mg, 0.61 mmol) in CH$_2$Cl$_2$(1 ml); after 2 h triethylamine (0.170 ml, 1.2 mmol), di-tert butoxycarbonate (130 mg, 0.60 mmol) and DMF (0.3ml) are added and the mixture is stirred at room temperature for 25 days. Concentration, partitioning between water and hexane, sonification filtration, re-concentration followed by purification by flash silica column chromatography (eluant 19:1 CH$_2$Cl$_2$: methanol) gives 8-(6-bromo-isoquinolin-4-ylmethyl)-3-isobutyl-1-methyl2,6dioxo-1,2,3,6-tetrahydro-purine-7-carboxylic acid .tert.-butyl ester ([MH]$^+$ 543). This intermediate (58 mg, 0.11 mmol) is added to Zn(CN)$_2$ (15 mg, 0.13 mmol) followed by 1,1'-bis(diphenylphosphino) ferrocene (9 mg), tris(dibenzylideneacetone) dipalladium(0) (5 mg) and anhydrous DMF (2.5 ml) and the resulting mixture stirred at 120° C. for 18 h and then for a further 24 h at 150° C. Zn(CN)$_2$ (57 mg, 0.49 mmol) and anhydrous DMF (1 ml) are then added and the mixture is heated for 2 h at 155° C. for 2 h followed by 18 h at 145° C. 1,1'-Bis (diphenylphosphino)ferrocene (9 mg), tris (dibenzylideneacetone)dipalladium(0) (9 mg) are then added and the reaction is heated for a further 6 h at 145° C. Concentration, trituration with water, filtration, washing with 1:1 saturated NaHCO$_3$/water, followed by extraction with CH$_2$Cl$_2$ and 1:1 methanol: CH$_2$Cl$_2$ and repetitive flash silica column chromatography (eluants 10:1 CH$_2$Cl$_2$:methanol then 20:1 CH$_2$Cl$_2$:methanol) gives 4-(3-isobutyl-1-methyl -2,6-dioxo-2,3,6,7-tetrahydro-1H-purin-8-ylmethyl)-isoquinoline-6-carbonitrile [MH]$^+$ 389.

Method N 1-(3-Dimethylaminopropyl)-3-ethylcarbodiimide hydrochloride (0.29 g, 1.9 mmol) is added to 5,6-diamino-1-isobutyl-3-methyl-1H-pyrimidine-2,4-dione (0.40 g, 1.9 mmol)) and (1-chloro-6,7-dimethoxy-isoquinolin-4-yl)-acetic acid (0.39 g, 1.78 mmol) in methanol and water and the mixture is stirred at ambient temperature for 2 hours. The methanol is evaporated and the resultant solid collected by filtration and recrystalised from ethylacetate/methanol. The resulting solid is heated in a sealed tube (100° C., 8 h) with 40% aqueous dimethylamine. The mixture is evaporated and extracted with ethylacetate. The ethylacetate solution is then washed with water and brine, dried over sodium sulphate, filtered and concentrated. Further purification by flash silica column chromatography (eluant: ethylacetate/methanol) yields 8-(1-dimethylamino-6,7-dimethoxy-isoquinolin-4-ylmethyl)3-isobutyl-1-methyl-3,7dihydro-purine-2,6-dione, MH$^+$ 467.

Method O 1-(3-Dimethylaminopropyl)-3-ethylcarbodiimide hydrochloride (0.29 g, 1.9 mmol) is added to 5,6-diamino-1-isobutyl-3-methyl-1H-pyrimidine-2,4-dione (0.40 g, 1.9 mmol)) and (1-chloro-6,7-dimethoxy-isoquinolin-4-yl)-acetic acid (0.39 g, 1.78 mmol) in methanol and water and the mixture is stirred at ambient temperature for 2 hours. The methanol is evaporated and the resultant solid collected by filtration and recrystalised from ethylacetate/methanol. The resulting solid is heated under reflux with piperidine for 8 h. The solution is filtered and the resulting solution washed with water and brine, dried over sodium sulphate, filtered and concentrated. Further purification by flash silica column chromatography (eluant: ethylacetate/methanol) yields a solid which is dissolved 20% 1N NaOH/methanol and heated to reflux for 2 h. Concentration, addition of water and extraction with ethyl acetate gives an organic fraction which is washed with water and brine, dried over Na2SO4, filtered and concentrated to give 8-(6,7-dimethoxy-1-piperidin-1-yl-isoquinolin-4-ylmethyl)-3-isobutyl-1-methyl-3,7-dihydro-purine-2,6-dione, MH$^+$ 507.

NMR Data for Examples ($^1$H 400 MHz DMSO-d6)

EXAMPLE 12

δ 325 (s 3H), 3.92 (s 3H), 4.02 (s 3H), 4.65 (s 2H), 7.70 (s 1H), 7.88 (s 1H), 8.45 (s 1H), 9.42 (s 1H), 11.1 (s 1H), 13.60 (s 1H)

EXAMPLE 13

δ 3.20 (s 3H), 4.95 (s 3H), 4.00 (s 3H), 4.52 (d J 4 2H), 4.70 (s 2H), 5.04 (d J 18 1H), 5.09 (d J 10 1H), 5.88 (m 1H), 7.60 (s 1H), 7.88 (s 1H), 8.46 (s 1H), 9.42 (s 1H), 13.7 (s 1H).

EXAMPLE 14

δ 0.20-0.40 (m 4H), 1.10-1.30 (m 1H), 3.21 (s 3H), 3.81 (m 2H), 3.98 (s 3H), 4.03 (s 3H), 4.66 (s 2H), 7.65 (s 1H), 7.85 (s 1H), 8.45 (s 1H), 9.39 (s 1H), 13.70 (s 1H).

EXAMPLE 15

δ 0.82 (s 9H), 3.20 (s 3H), 3.78 (s 2H), 3.99 (s 3H), 4.04 (s 3H), 7.62 (s 1H), 7.90 (s 1H), 8.45 (s 1H), 9.44 (s 1H), 13.60 (s 1H).

EXAMPLE 16

δ 0.81 (d J 7 12H), 1.98 (m 1H), 2.12 (m 1H), 3.70 (d J 8 2H), 3.78 (d J 7 2H), 3.99 (s 3H), 4.05 (s 3H), 4.70 (s 2H), 7.65 (s 1H), 7.90 (s 1H), 8.46 (s 1H), 9.45 (s 1H), 13.6 (s 1H).

EXAMPLE 17

δ 0.80-1.10 (m 6H), 1.40-1.60 (m 4H), 1.80 (m 1H), 3.15 (s 1H), 3.76 (d J 8 2H), 3.91 (s 3H), 4.02 (s 3H), 4.68 (s 2H), 7.60 (s 1H), 7.88 (s 1H), 8.44 (s 1H), 13.60 (s 1H).

EXAMPLE 18

δ 1.69 (s 3H), 3.21 (s 3H), 3.98 (s 3H), 4.01 (s 3H), 4.46 (s 2H), 4.52 (s 1H), 4.68 (s 2H), 4.76 (s 1H), 7.58 (s 1H), 7.84 (s 1H), 8.45 (s 1H), 9.42 (s 1H), 13.60 (s 1H).

EXAMPLE 19

δ 1.50-1.85 (m 4H), 3.18 (s 3H), 3.50-3.85 (m 4H), 3.95 (s 3H), 4.10-4.20 (m 1H), 4.70 (s 2H), 7.75 (s 1H), 7.920 (s 1H), 8.50 (s 1H), 9.50 (s 1H), 13.60 (br s 1H).

EXAMPLE 20

δ 0.70-0.80 (m 6H), 0.99-1.10 (m 1H), 1.20-1.25 (m 1H), 1.88-2.00 (m 1H), 3.21 (s 3H), 3.64-3.80 (m 2H), 3.95 (s 3H), 4.00 (s 3H), 4.68 (s 2H), 7.60 (s 1H), 7.80 (s 1H), 8.45 (s 1H), 9.42 (s 1H), 13.60 (br s 1H).

EXAMPLE 21

δ 0.83 (t J 8 3H), 1.63 (sextet J 8 2H), 3.83 (t J 8 2H), 3.99 (s 3H), 4.05 (s 3H), 4.69 (s 2H), 7.64 (s 1H), 7.88 (s 1H), 8.44 (s 1H), 9.42 (s 1H), 11.10 (s 1H), 13.60 (s 1H).

EXAMPLE 23

δ 0.80 (d J 7 6H), 3.18 (s 3H), 3.75 (d J 8 2H), 4.60 (s 2H), 6.32 (s 2H), 7.71 (s 1H), 7.82 (s 1H), 8.50 (s 1H), 9.42 (s 1H), 13.50 (s 1H).

EXAMPLE 49

δ 0.12-0.25 (m 4H), 1.02-1.10 (m 1H), 3.26 (s 3H), 3.68 (d J 7 2H), 4.00 (s 3H), 4.80 (s 2H), 7.70 (d J 9 1H), 8.21 (d J 9 1H), 8.38 (s 1H), 9.20 (s 1H), 13.10 is 1H).

EXAMPLE 86

3-Isobutyl-1-methyl-8-[1-(6-methyl-5-oxo-5,6-dihydro-[1,3]dioxolo[4,5-.g.]isoquinolin-8-yl)-ethyl]-3,7-dihydro-purine-2,6dione Benzo[1,3]dioxol-5-ylmethyl-(2,2-dimethoxy-ethyl)-amine (Tetrahedron 1968, 24, 1467) is treated with pyruvic acid according to the general procedure for Intermediate 22 to afford 2-[1,3]dioxolo[4,5-.g.]isoquinolin-8-yl-propionic acid hydrochloride, mp 224-226° C. Treatment with HCl gas in ethanol affords the corresponding ethyl ester hydrochloride, mp 223-225° C. A solution of this compound (2.73 g, 10 mmol) in benzene (20 ml) is treated with dimethyl sulfate (1.26 g, 10 mmol), stirred at room temperature for 5 hours and the solvent is evaporated. The crude oil is dissolved in water (20 ml), cooled to 0-5° C. and a solution of $K_3Fe(CN)_6$ (5.72 g, 17.4 mmol) in water (25 ml) and sodium hydroxide (2.04 g, 51 mmol) in water (15 ml) are added. After 1.5 hours at 5° C., the reaction is adjusted to pH 2 with concentrated hydrochloric acid and the product collected by filtration then crystallised from methanol-dichloromethane to afford 2-(6-methyl-5-oxo-5,6-dihydro-[1,3]dioxolo[4,5-.g.]isoquinolin-8-yl)-propionic acid, mp 290° C. (dec). This intermediate is then converted to the xanthine according to the general procedure of Method D, [MH]$^+$ 452.

EXAMPLE 87

8-(6,7-Dimethoxy-quinolinyl-ylmethyl)-3-isobutyl-1-methyl-3,7-dihydro-purine-2,6-dione Lithium diisopropylamide (2M pentane solution 2.46 ml, 4.92 mmol) and potassium t-butoxide (0.552 g, 4.92 mmol) are added to THF (10 ml) at −70° C., followed by 6,7-dimethoxy-4-methyl-quinoline[J. Org. Chem., 1997, 623, 568] (1.0 g, 4.92 mmol). After 1 hour the reaction is poured on to an excess of crushed dry ice and warmed to room temperature overnight. Pyridine hydrochloride (0.57 g, 4.92 mmol) is added and the reaction partitioned between ether and water. The aqueous phase is evaporated, taken into hot methanol, treated with charcoal, filtered through celite and evaporated to afford (6,7-dimethoxy-quinolinyl-4-yl)-acetic acid, $MH^+$ 248. This intermediate is then converted to the xanthine according to the general procedure of Method C, mp>250° C.

What is claimed is:

1. A method of treating stable, unstable and variant (Prinzmetal) angina, hypertension, pulmonary hypertension, congestive heart failure, atherosclerosis, conditions of reduced blood vessel patency, or peripheral vascular disease comprising administering a therapeutically effective amount of a pharmaceutical composition comprising a compound of formula

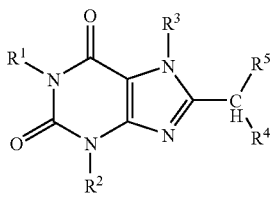

I in free or salt form, wherein $R^1$ is hydrogen or alkyl optionally substituted by hydroxy, alkoxy, or alkylthio, $R^2$ is hydrogen, alkyl, hydroxyalkyl, alkylcarbonyloxy-alkyl, alkoxyalkyl, alkylthioalkyl, alkenyl, cycloalkylalkyl, heterocyclylalkyl, aralkyl in which the aryl ring thereof is optionally fused to a 5-membered heterocyclic group or is optionally substituted by one or more substituents selected from alkoxy, amino, alkylamino, dialkylamino, acylamino, halogen, hydroxy, aminosulfonyl, alkylaminosulfonyl, dialkylaminosulfonyl, alkylsulfonylamino or dialkylaminosulfonylamino, $R^3$ is hydrogen or alkyl optionally substituted by hydroxy, alkoxy, or alkylthio, $R^4$ is hydrogen or alkyl, $R^5$ is a quinolinyl, isoquinolinyl or oxodihydroisoquinolinyl group optionally fused to a 5-membered heterocyclic group and optionally substituted by one or more substituents selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —$N(R^6)R^7$, aryl optionally substituted by one or more substituents selected from halogen or alkoxy, or heteroaryl having 5 or 6 ring atoms attached through a ring carbon atom to the indicated carbon atom, and $R^6$ and $R^7$ are each independently hydrogen or alkyl optionally substituted by hydroxy or alkoxy or one of $R^6$ and $R^7$ is hydrogen and the other is acyl, or $R^6$ and $R^7$ together with the nitrogen atom to which they are attached denote a 5- or 6-mambered heterocyclyl group.

2. The method of claim 1 wherein the compound of formula is 3-isobutyl-8-(6-methoxy-isoquinolin-4-ylmethyl)-1-methyl-3, 7-dihydro-purine-2,6-dione.

3. The method of claim 1 wherein a condition of reduced blood vessel patency is post-percutaneous transluminal coronary angioplasty.

* * * * *